(12) United States Patent
DeVries et al.

(10) Patent No.: US 9,675,352 B2
(45) Date of Patent: Jun. 13, 2017

(54) DEVICES AND METHODS FOR FASTENING TISSUE LAYERS

(71) Applicant: Boston Scientific Scimed, Inc., Maple Grove, MN (US)

(72) Inventors: Robert DeVries, Northborough, MA (US); William J. Shaw, Cambridge, MA (US); Kristian DiMatteo, Waltham, MA (US); Gerhard Buess, Tubingen Bebenhausen (DE); Daniel Kalanovic, Munich (DE); Marc Schurr, Tuebingen (DE); Roy Sullivan, Uxbridge, MA (US); Marc Tassy, Jr., Framingham, MA (US); John Griego, Blackstone, MA (US); Patrick Gutileus, Monroe, CT (US); Paul DiCesare, Easton, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 163 days.

(21) Appl. No.: 14/245,081

(22) Filed: Apr. 4, 2014

(65) Prior Publication Data

US 2014/0222030 A1 Aug. 7, 2014

Related U.S. Application Data

(63) Continuation of application No. 12/907,172, filed on Oct. 19, 2010, now Pat. No. 8,728,104, which is a
(Continued)

(51) Int. Cl.
*A61B 17/08* (2006.01)
*A61B 17/10* (2006.01)
(Continued)

(52) U.S. Cl.
CPC .......... *A61B 17/08* (2013.01); *A61B 17/0401* (2013.01); *A61B 17/068* (2013.01);
(Continued)

(58) Field of Classification Search
CPC ......... A61B 17/08; A61B 17/10; A61B 17/29; A61B 17/0401; A61B 17/06109;
(Continued)

(56) References Cited

U.S. PATENT DOCUMENTS

| 4,243,040 A | 1/1981 | Beecher |
| 4,593,699 A | 6/1986 | Poncy et al. |

(Continued)

FOREIGN PATENT DOCUMENTS

| EP | 0452123 | 10/1991 |
| EP | 1129674 | 9/2001 |

(Continued)

OTHER PUBLICATIONS

U.S. Appl. No. 09/920,809, filed Aug. 3, 2001.
(Continued)

*Primary Examiner* — Julian W Woo
(74) *Attorney, Agent, or Firm* — Bookoff McAndrews, PLLC

(57) ABSTRACT

Endoscopic devices and methods used for fastening multiple tissue layers, such as, for example, an endoscopic fundoplication procedure, are disclosed. The device may include, for example, an elongated tubular member having a proximal end for extending outside of the body and a distal end for positioning proximate the multiple tissue layers, a grasper configured for positioning proximate the distal end of the tubular member and for grasping at least one of the multiple tissue layers, a device coupled to the distal end of the tubular member for folding the multiple tissue layers together, a tissue fastener configured to be inserted into the tissue layers
(Continued)

to hold the tissue layers together, and a fastener head for inserting the tissue fastener into the tissue layers.

15 Claims, 42 Drawing Sheets

Related U.S. Application Data continuation of application No. 11/471,513, filed on Jun. 21, 2006, now Pat. No. 7,837,698, which is a continuation of application No. 10/230,682, filed on Aug. 29, 2002, now Pat. No. 7,083,630.

(51) Int. Cl.
| | |
|---|---|
| A61B 17/04 | (2006.01) |
| A61B 17/06 | (2006.01) |
| A61B 17/068 | (2006.01) |
| A61B 17/29 | (2006.01) |
| A61B 1/273 | (2006.01) |
| A61B 17/064 | (2006.01) |
| A61B 17/30 | (2006.01) |
| A61B 17/00 | (2006.01) |

(52) U.S. Cl.
CPC ........ *A61B 17/06109* (2013.01); *A61B 17/10* (2013.01); *A61B 17/29* (2013.01); *A61B 1/2736* (2013.01); *A61B 17/0469* (2013.01); *A61B 17/0487* (2013.01); *A61B 17/0643* (2013.01); *A61B 2017/00827* (2013.01); *A61B 2017/0404* (2013.01); *A61B 2017/0417* (2013.01); *A61B 2017/0419* (2013.01); *A61B 2017/0445* (2013.01); *A61B 2017/0458* (2013.01); *A61B 2017/0461* (2013.01); *A61B 2017/0462* (2013.01); *A61B 2017/0464* (2013.01); *A61B 2017/061* (2013.01); *A61B 2017/081* (2013.01); *A61B 2017/306* (2013.01)

(58) Field of Classification Search
CPC ............ A61B 17/068; A61B 2017/081; A61B 2017/00827; A61B 17/0643; A61B 17/0469; A61B 17/0487; A61B 2017/0404; A61B 2017/0417; A61B 2017/0458; A61B 2017/061; A61B 2017/046; A61B 2017/0445; A61B 2017/0419; A61B 2017/306; A61B 2017/0461; A61B 2017/0464; A61B 1/2736

See application file for complete search history.

(56) References Cited

U.S. PATENT DOCUMENTS

| | | | |
|---|---|---|---|
| 4,646,722 A | 3/1987 | Silverstein et al. | |
| 4,741,326 A | 5/1988 | Sidall et al. | |
| 4,772,275 A | 9/1988 | Erlich | |
| 4,886,049 A | 12/1989 | Darras | |
| 4,936,304 A | 6/1990 | Kresh et al. | |
| 4,946,440 A | 8/1990 | Hall | |
| 5,080,663 A | 1/1992 | Mills et al. | |
| 5,088,178 A | 2/1992 | Stolk | |
| 5,088,979 A | 2/1992 | Filipi et al. | |
| 5,091,205 A | 2/1992 | Fan | |
| 5,228,851 A | 7/1993 | Burton | |
| 5,234,443 A | 8/1993 | Phan et al. | |
| 5,329,935 A | 7/1994 | Takahashi | |
| 5,364,345 A | 11/1994 | Lowery et al. | |
| 5,403,326 A * | 4/1995 | Harrison ............ | A61B 17/0643 606/151 |
| 5,415,157 A | 5/1995 | Welcome | |
| 5,423,830 A | 6/1995 | Schneebaum et al. | |
| 5,571,116 A | 11/1996 | Bolanos et al. | |
| 5,593,424 A * | 1/1997 | Northrup, III ..... | A61B 17/0401 606/232 |
| 5,599,300 A | 2/1997 | Weaver et al. | |
| 5,647,857 A | 7/1997 | Anderson et al. | |
| 5,695,448 A | 12/1997 | Kimura et al. | |
| 5,733,294 A | 3/1998 | Forber et al. | |
| 5,765,682 A | 6/1998 | Bley et al. | |
| 5,797,943 A | 8/1998 | Danks et al. | |
| 5,938,586 A | 8/1999 | Wilk et al. | |
| 5,976,127 A | 11/1999 | Lax | |
| 6,027,480 A | 2/2000 | Davis et al. | |
| 6,051,293 A | 4/2000 | Weilandt | |
| 6,074,401 A * | 6/2000 | Gardiner ............ | A61B 17/0625 606/139 |
| 6,086,600 A | 7/2000 | Kortenbach | |
| 6,113,609 A | 9/2000 | Adams | |
| 6,224,543 B1 | 5/2001 | Gammons et al. | |
| 6,231,561 B1 | 5/2001 | Frazier et al. | |
| 6,293,909 B1 | 9/2001 | Chu et al. | |
| 6,312,437 B1 | 11/2001 | Kortenbach | |
| 6,352,503 B1 | 3/2002 | Matsui et al. | |
| 6,425,900 B1 | 7/2002 | Knodel et al. | |
| 6,491,714 B1 | 12/2002 | Bennett | |
| 6,494,888 B1 | 12/2002 | Laufer et al. | |
| 6,551,315 B2 | 4/2003 | Kortenbach et al. | |
| 6,689,130 B2 | 2/2004 | Arai et al. | |
| 6,736,828 B1 | 5/2004 | Adams et al. | |
| 6,749,601 B2 | 6/2004 | Chin | |
| 7,125,413 B2 * | 10/2006 | Grigoryants ....... | A61B 17/0469 606/139 |
| 7,371,215 B2 | 5/2008 | Colliou et al. | |
| 8,057,494 B2 * | 11/2011 | Laufer ............... | A61B 17/0057 227/175.1 |
| 8,241,308 B2 * | 8/2012 | Kortenbach ....... | A61B 17/0643 606/151 |
| 8,728,104 B2 * | 5/2014 | DeVries ........... | A61B 17/06109 606/153 |
| 2001/0037130 A1 | 11/2001 | Adams | |
| 2001/0049499 A1 | 12/2001 | Lui et al. | |
| 2002/0156344 A1 | 10/2002 | Pasricha et al. | |
| 2003/0220660 A1 | 11/2003 | Kortenbach et al. | |
| 2004/0044364 A1 | 3/2004 | DeVries et al. | |
| 2004/0087976 A1 | 5/2004 | DeVries et al. | |
| 2006/0241661 A1 | 10/2006 | DeVries et al. | |

FOREIGN PATENT DOCUMENTS

| | | |
|---|---|---|
| JP | 2000-279418 | 10/2000 |
| JP | 2002-238913 | 8/2002 |
| WO | WO 99/22649 | 5/1999 |
| WO | WO 99/33402 | 7/1999 |
| WO | WO 00/78227 A1 | 12/2000 |
| WO | WO 01/35834 A1 | 5/2001 |
| WO | WO 01/95818 A1 | 12/2001 |
| WO | WO 02/17771 A2 | 3/2002 |
| WO | WO 02/24080 | 3/2002 |
| WO | WO 02/28289 A1 | 4/2002 |
| WO | WO 02/30335 A2 | 4/2002 |

OTHER PUBLICATIONS

U.S. Appl. No. 10/230,672, filed Aug. 29, 2002.
Lightdale, Charles J., M.D., "Gastroesophageal Reflux Disease: New Endoscopic Treatments," *Digestive Disease Week 2001*, Atlanta Ga.
Mason, Rodney J. et al., "Per Oral Endoscopic Nissen Fundoplication: The Introduction of a New Era," *Digestive Disease Week 2001*, Atlanta, Ga.
PCT Invitation to Pay Additional Fees (Form PCT/ISA/206 entitled "Communication Relating to the Results of the Partial International Search") for PCT Application No. PCT/US 03/24794, mailed Feb. 12, 2004.

\* cited by examiner

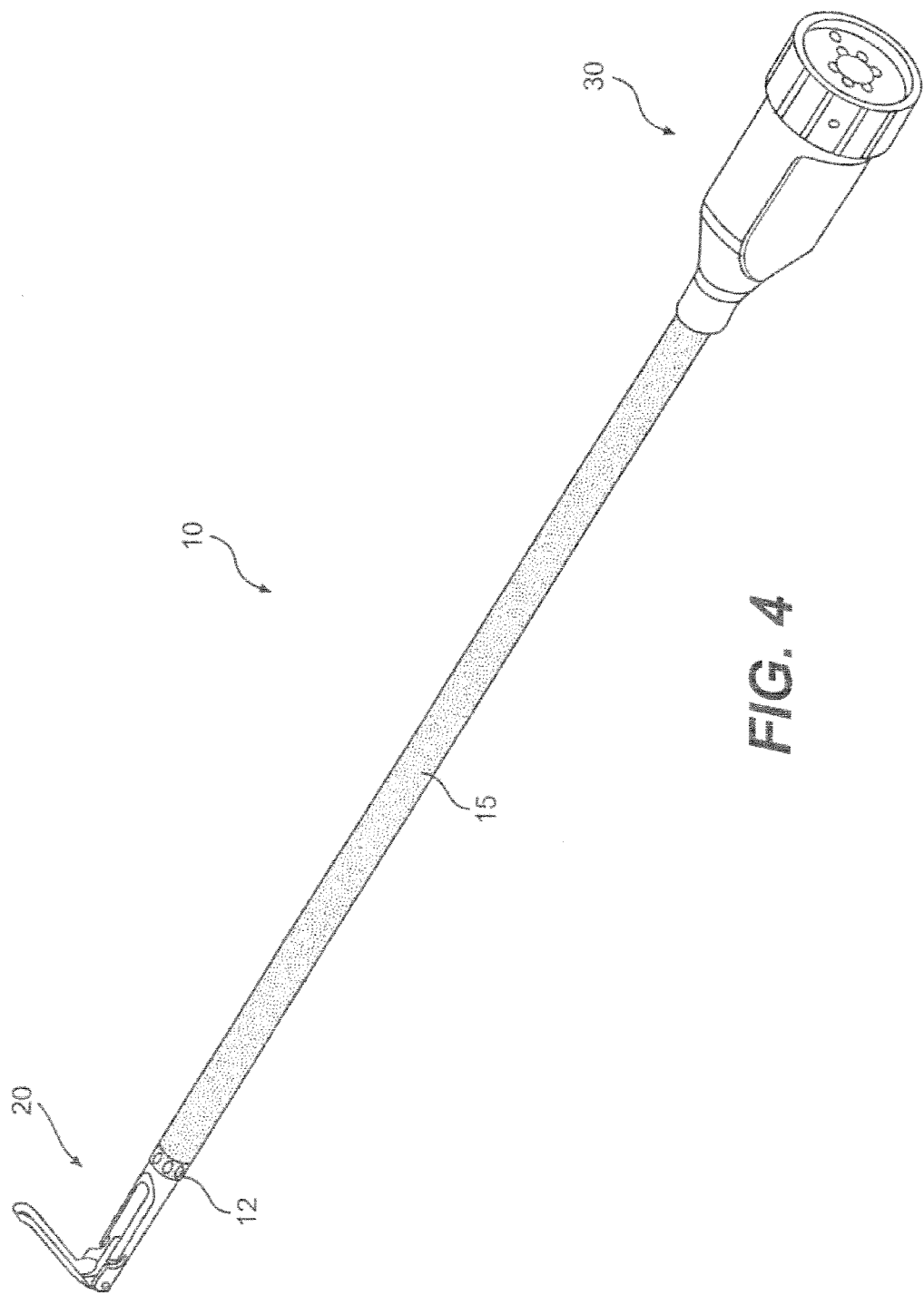

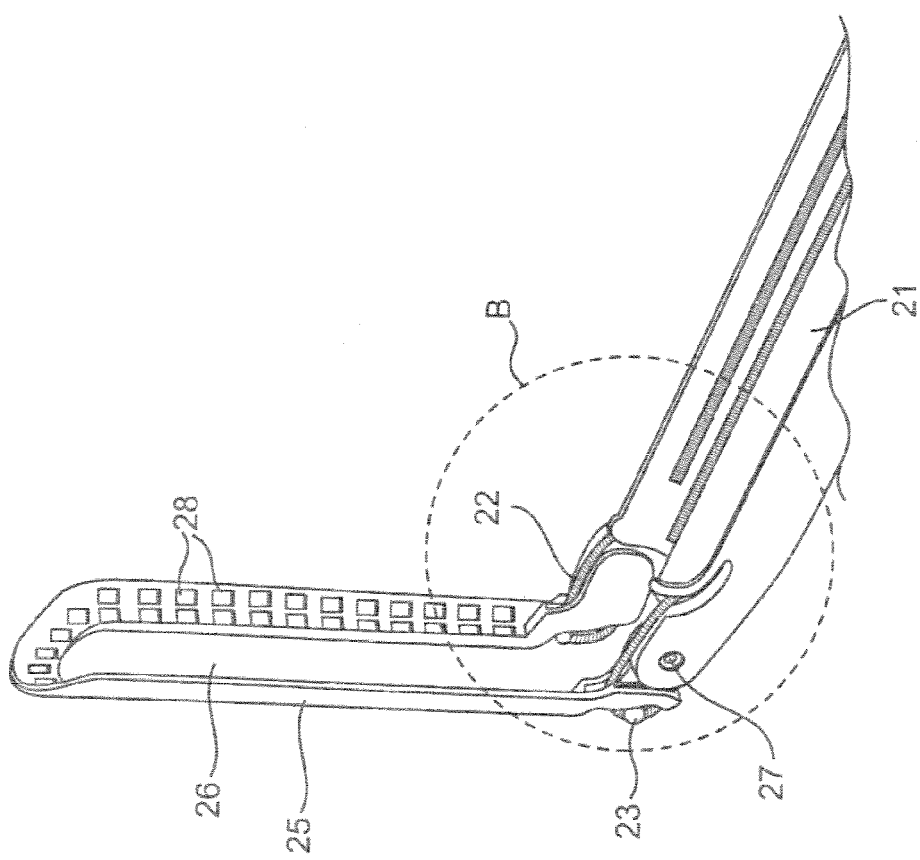

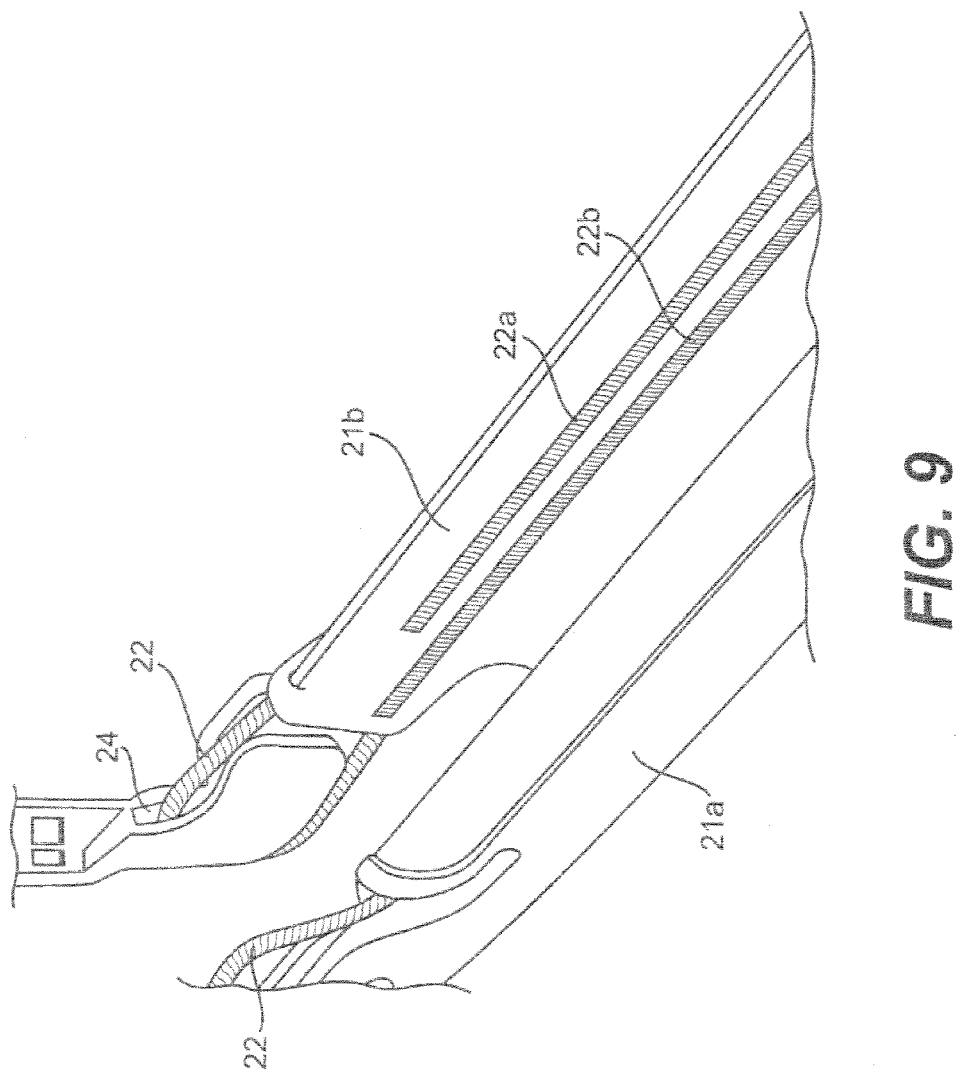

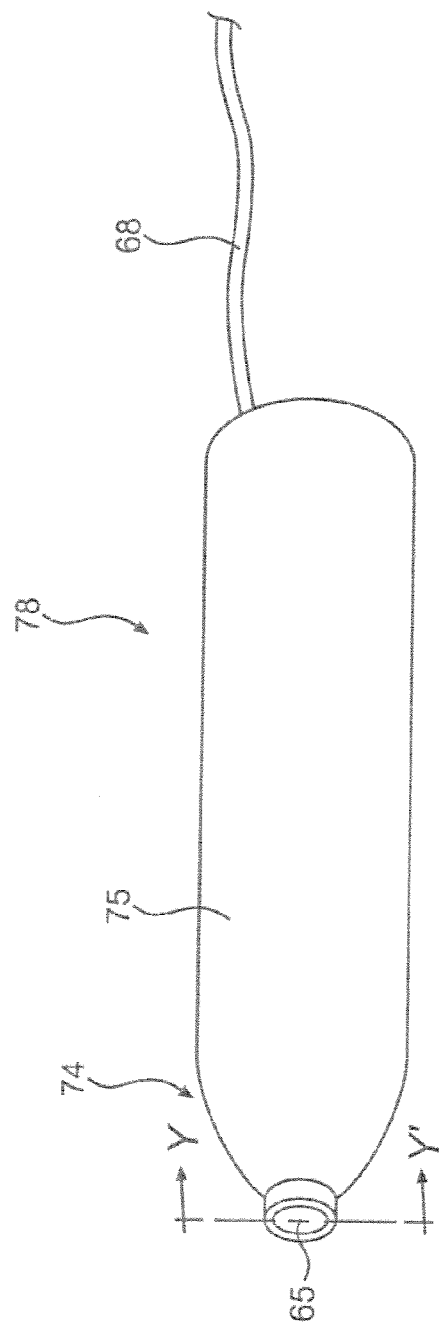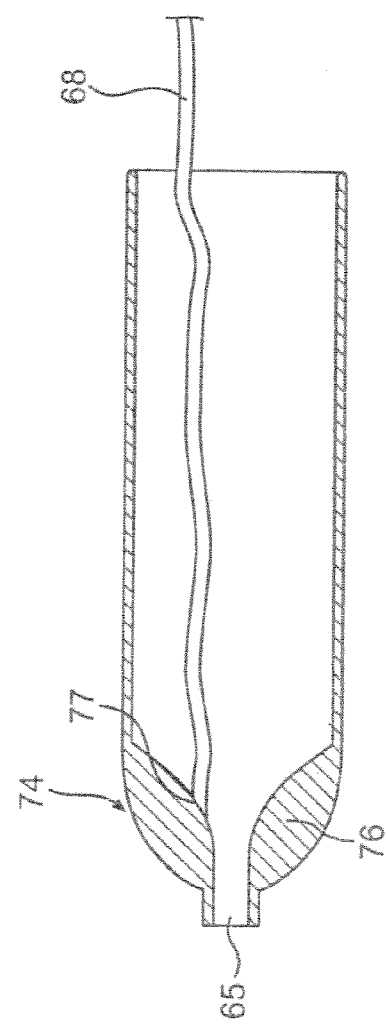
FIG. 23A
FIG. 23B

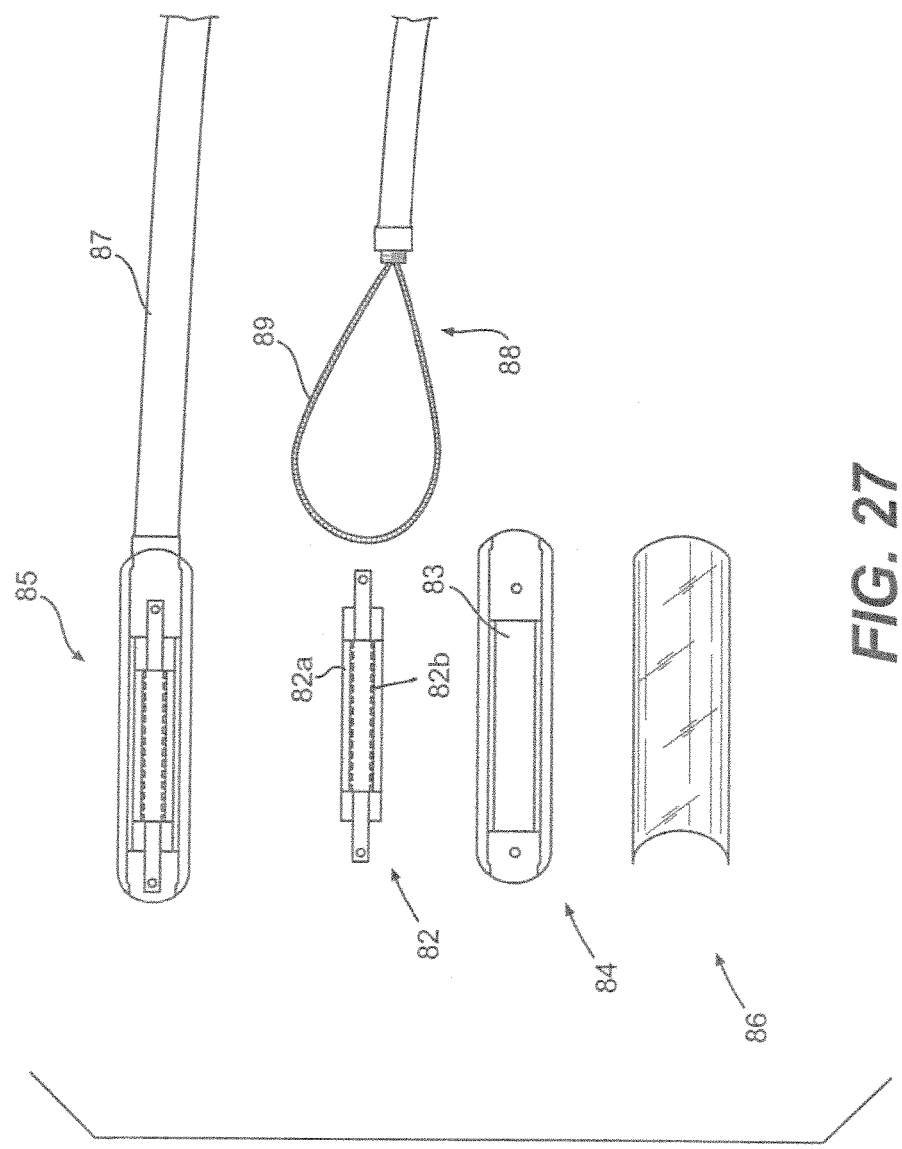

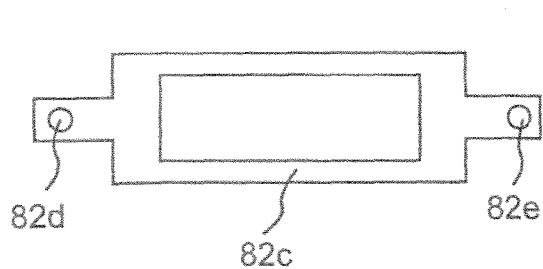
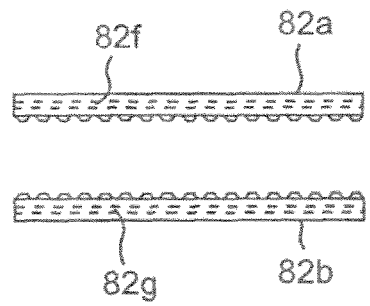
FIG. 27A  FIG. 27B
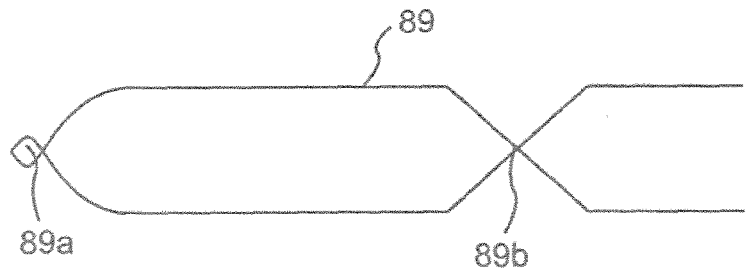
FIG. 27C
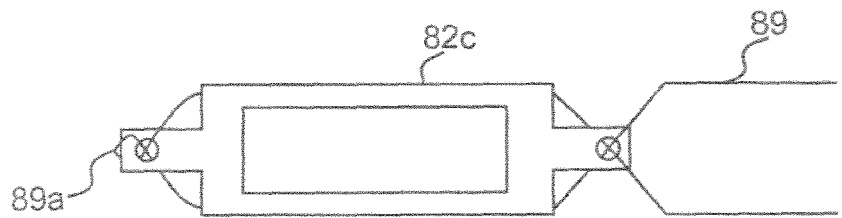
FIG. 27D

DEVICES AND METHODS FOR FASTENING TISSUE LAYERS

CROSS-REFERENCE TO RELATED APPLICATIONS

This is a continuation of U.S. application Ser. No. 12/907,172, filed Oct. 19, 2010, now U.S. Pat. No. 8,728,104, which is a continuation of U.S. application Ser. No. 11/471,513, filed Jun. 21, 2006, now U.S. Pat. No. 7,837,698, which is a continuation of U.S. application Ser. No. 10/230,682, filed Aug. 29, 2002, now U.S. Pat. No. 7,083,630, all of which are incorporated by reference herein in their entireties.

This application relates to commonly assigned U.S. application Ser. No. 10/230,672 of Robert DeVries et al., filed on Aug. 29, 2002, published as U.S. Publication No. 2004/0044364 A1, and entitled "TISSUE FASTENERS AND RELATED DEPLOYMENT SYSTEMS AND METHODS." This application also relates to commonly assigned U.S. application Ser. No. 09/920,809 of Yem Chin, filed on Aug. 3, 2001, now U.S. Pat. No. 6,749,601, and entitled "PROTECTIVE SLEEVE FOR AN ENDOSCOPIC INSTRUMENT AND RELATED METHOD OF USE." The complete disclosures of these applications are incorporated by reference herein.

DESCRIPTION OF THE INVENTION

Field of the Invention

The present invention relates to endoscopic devices and related methods. In particular, the present invention relates to endoscopic devices and methods used in, for example, a tissue fundoplication procedure for treatment of Gastroesophageal Reflux Disease (GERD).

Background of the Invention

Gastroesophageal reflux occurs when stomach acid enters the esophagus. This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions and changes in tissue structure that result from reflux of stomach acid into the esophagus are referred to generally as Gastroesophageal Reflux Disease (GERD).

Many mechanisms contribute to prevent gastroesophageal reflux in healthy individuals. One such mechanism is the functioning of the lower esophageal sphincter (LES). With reference to FIG. 1, the LES 2 is a ring of smooth muscle and increased annular thickness existing in approximately the last four centimeters of the esophagus. In its resting state, the LES creates a region of high pressure (approximately 15-30 mm Hg above intragastric pressure) at the opening of the esophagus 3 into the stomach 7. This pressure essentially closes the esophagus 3 so that contents of the stomach cannot pass back into the esophagus 3. The LES 2 opens in response to swallowing and peristaltic motion in the esophagus, allowing food to pass into the stomach. After opening, however, a properly functioning LES 2 should return to the resting, or closed state. Transient relaxations of the LES 2 do occur in healthy individuals, typically resulting in occasional bouts of heartburn.

The physical interaction occurring between the gastric fundus 5 and the esophagus 3 also prevents gastroesophageal reflux. The gastric fundus 5 is a lobe of the stomach situated at the top of the stomach 7 distal to the esophagus 3. In asymptomatic individuals, the fundus 5 presses against the opening of the esophagus 3 when the stomach 7 is full of food and/or gas. This effectively closes off the esophageal opening to the stomach 7 and helps to prevent acid reflux back into the esophagus 3. More specifically, as the food bolus is immersed in gastric acid, it releases gas which causes the fundus 5 of the stomach 7 to expand and thereby exert pressure on the distal esophagus 3 causing it to collapse. The collapse of the esophagus lumen reduces the space for the stomach acid to splash past the closed esophagus lumen and thereby protect the proximal esophagus from its destructive contact.

In individuals with GERD, the LES 2 functions abnormally, either due to an increase in transient LES relaxations, decreased muscle tone of the LES 2 during resting, or an inability of the esophageal tissue to resist injury or repair itself after injury. These conditions often are exacerbated by overeating, intake of caffeine, chocolate or fatty foods, smoking, and/or hiatal hernia. Avoiding these exacerbating mechanisms helps curb the negative side effects associated with GERD, but does not change the underlying disease mechanism.

A surgical procedure, known generally as fundoplication, has been developed to prevent acid reflux in patients whose normal LES functioning has been impaired, either as a result of GERD or other adverse effects. This procedure involves bringing the fundus wall 6 into closer proximity of the esophageal wall 4 to help close off the esophageal opening into the stomach 7, as shown in FIG. 2. Traditionally, this procedure has been performed as an open surgery, but also has been performed laparoscopically.

As with any surgery, the attendant risks are great. Due to relatively large incisions necessary in the performance of open surgery, relatively large amount of blood is lost, the risk of infection increases, and the potential for post-operative hernias is high. Further, the relatively large incisions necessary in the performance of open surgery require extended recovery times for the incision to heal.

A laparoscopic procedure may involve performing laparotomies for trocar ports (penetrations of the abdominal wall), percutaneous endoscopic gastronomies (incisions through the skin into the stomach), and the installation of ports through which, for example, a stapler, an endoscope, and an esophageal manipulator (invagination device) are inserted. Under view of the endoscope, the esophageal manipulator is used to pull the interior of the esophagus 3 into the stomach 7. When the esophagus is in position, with the fundus 5 of the stomach plicated, the stapler is moved into position around the lower end of the esophagus and the plicated fundus is stapled to the esophagus 3. The process may be repeated at different axial and rotary positions until the desired fundoplication is achieved. This procedure is still relatively invasive requiring incisions through the stomach, which has a risk of infection. The location of the incision in the abdominal wall presents a risk of other negative effects, such as sepsis, which can be caused by leakage of septic fluid contained in the stomach.

SUMMARY OF THE INVENTION

Therefore, it is accordingly an object of the present invention to provide less invasive devices and methods for performing the fundoplication procedure. This is achieved by utilizing fundoplication devices which can be endoluminally delivered through the esophagus, thereby eliminating the need for highly invasive, physiologically insulting surgical procedures.

To attain the advantages and in accordance with the purpose of the invention, as embodied and broadly described herein, one aspect of the invention provides a system for fastening multiple tissue layers of a body. The system may include various components, including, for example, an elongated tubular member having a proximal end for extending outside of the body and a distal end for positioning proximate the multiple tissue layers, a grasper configured for positioning proximate the distal end of the tubular member and for grasping at least one of the multiple tissue layers, a device coupled to the distal end of the tubular member for folding the multiple tissue layers together, a tissue fastener configured to be inserted into the tissue layers to hold the tissue layers together, and a fastener head for inserting the tissue fastener into the tissue layers. According to another aspect, the invention includes related methods of using these various components to insert a tissue fastener and fasten multiple tissue layers together.

According to a further aspect, the invention includes a device for folding together multiple tissue layers of a body. The device may include an elongated tube having a proximal end for extending outside of the body and a distal end for positioning proximate the multiple tissue layers, an actuation handle coupled to the proximal end of the tube, and a distal body coupled to the distal end of the tube, the distal body including a fixed portion and a folding arm pivotally connected to the fixed portion, and an elongate member extending through the tube to connect the handle and the folding arm. Rotation of at least a portion of the handle causes translation of the elongate member to pivot the folding arm from a closed position to an open position. According to another aspect, the invention includes related methods of using such a device to fold multiple tissue layers together.

According to yet another aspect, the invention includes a device for protecting a lumen of a body during an endoluminal delivery of a surgical device. The device may include a substantially cylindrical, inflatable balloon defining an internal space along at least a portion of a length of the balloon for accepting the surgical device, a handle having a port for connection to a source of inflating fluid, and a hollow, elongate tube connecting the port to the balloon. According to another aspect, the invention includes related methods of using a protection device for protecting a body lumen during insertion of a surgical device.

According to an even further aspect, the invention includes a device for grasping tissue of a body. The device may include an elongated tube having a proximal end for extending outside of the body and a distal end for positioning proximate tissue, an actuation handle coupled to the proximal end of the tube and including a connection for connecting to a vacuum source, and a distal body coupled to the distal end of the tube and including a distal head defining an opening in fluid communication with the vacuum source and jaws for grasping tissue received in the opening by suction. According to another aspect, the invention includes related methods of using the grasping device for grasping tissue.

According to a still further aspect, the invention includes a device for delivering a tissue fastener to multiple tissue layers. The device may include an elongated tube having a proximal end for extending outside of the body and a distal end for positioning proximate the multiple tissue layers, a head coupled to the distal end of the tube and having a slot to hold a tissue fastener, and a needle configured to extend through a lumen of the tube to and through a curved groove in the head leading to the slot. According to another aspect, the invention includes related methods of using the delivery device for delivering a tissue fastener to and into the tissue layers.

According to another aspect, the invention includes a method of fastening multiple tissue layers together that includes the steps of inserting an elongated tubular member into a body passage so that a distal end of the tubular member is proximate the tissue layers, positioning a grasper proximate the distal end of the tubular member, grasping at least one of the multiple tissue layers, folding the multiple tissue layers together by a distal body of the tubular member, and inserting a tissue fastener into the tissue layers to hold the tissue layers together.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

In the drawings:

FIG. 4 is a perspective view of an A-frame device, according to an embodiment of the present invention;

FIG. 8 is a perspective view of the A-frame head, shown in FIGS. 5-7, with the folding arm in an open position;

FIG. 9 is an enlarged view of section B of FIG. 8;

FIG. 23A is a perspective view of a protection device, according to still another embodiment of the present invention;

FIG. 23B is a cross-sectional view of the protection device shown in FIG. 23A along the Y-Y' plane of FIG. 23A;

FIGS. 26-27 are top and bottom views, respectively, of a grasper head, according to an embodiment of the present invention, showing various components;

FIGS. 27A-D are schematic illustration of a connection method between an operating cable and a pair of jaws, according to an embodiment of the present invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 1:
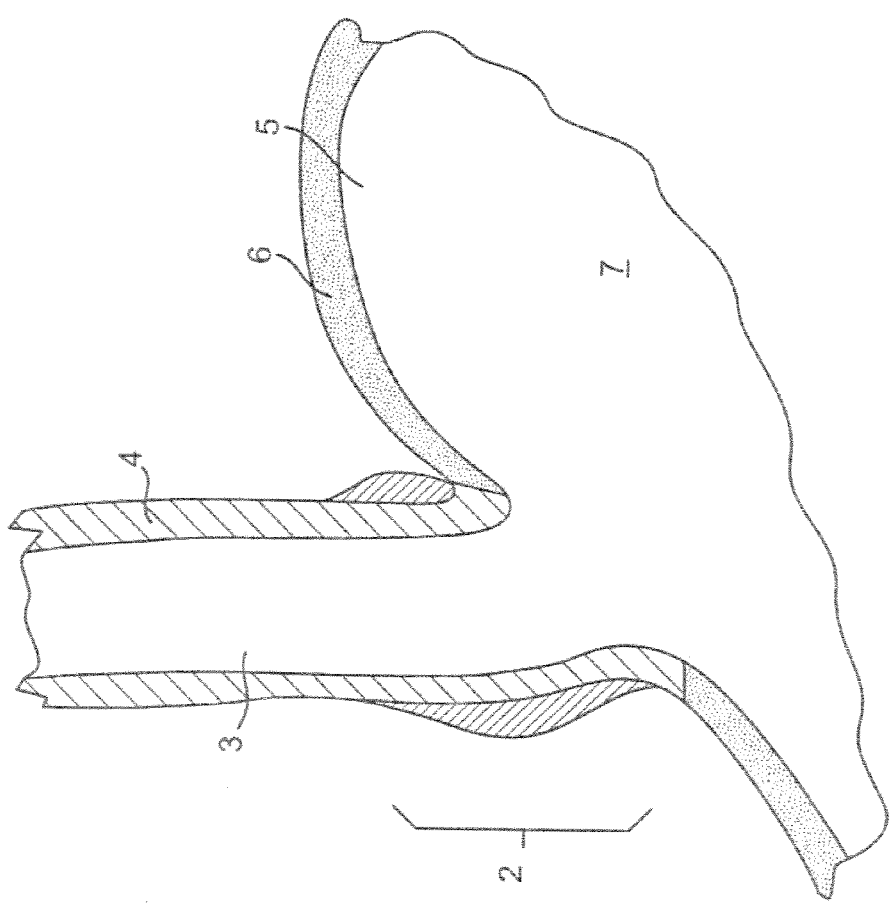
FIG. 1 is a cross-sectional view of the gastrointestinal tract in the region of the lower esophageal sphincter (LES) and the fundus of the stomach.
Figure 3:
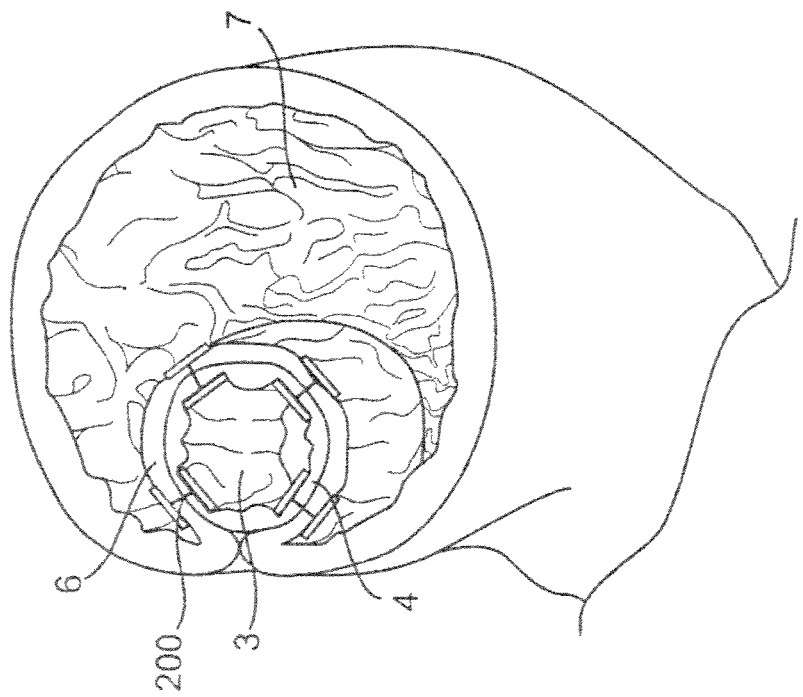
FIG. 3 is a perspective view of the gastrointestinal tract in the region of the lower esophageal sphincter (LES) and the fundus of the stomach, showing the cross-sectional view of the A-A' plane of FIG. 2 after a fundoplication procedure is performed.
Figure 2:
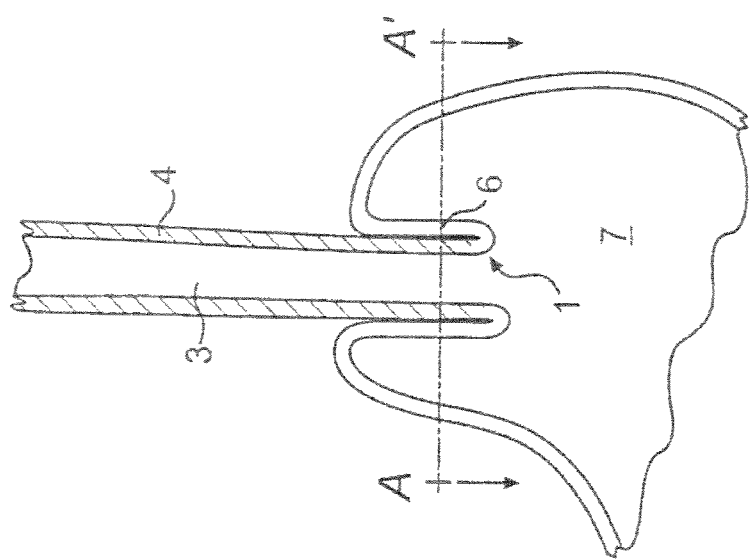
FIG. 2 is a cross-sectional view of the gastrointestinal tract in the region of the lower esophageal sphincter (LES) and the fundus of the stomach, after a fundoplication procedure is performed.

A newly developed form of fundoplication, referred to as endoscopic fundoplication, is an endoluminal procedure in which the fundus wall 6 is folded back onto the esophagus wall 4 and wraps around the esophagus 3, as shown in FIGS. 2 and 3. The tissue fold 1 formed between the esophagus 3 and the fundus 5 then is secured by a suitable fastening means, such as, for example, a plurality of double T-fasteners 200, shown in FIG. 3. The endoscopic fundoplication may be performed as an endoluminal procedure in which insertion of required medical instruments occurs through the esophagus 3. Such a procedure has the benefits of being less invasive, quicker, and less expensive as compared to previous techniques.

An endoluminal system used in, for example, a fundoplication procedure, according to an embodiment of the present invention, may include a number of individual components. These components may include an A-frame device, a protection device, an invagination device, a fastener delivery system, and at least one tissue fastener, each of which will be described separately in the following subsections.

A-Frame Device

FIG. 4 shows an A-frame device 10 according to an embodiment of the present invention. The A-frame device 10 includes an A-frame head 20, an A-frame handle 30, and a downtube 15. The A-frame head 20 and the A-frame handle 30 are each connected to the downtube 15 via a distal adapter 12 and a proximal adapter, respectively, both of which will be shown and described further herein. The downtube 15 can extend from outside of a body to a site deep within the body, and is sufficiently flexible to traverse through tortuous paths within a body, such as, for example, to the gastroesophageal junction site. The downtube 15 contains a plurality of lumens, also to be described further herein, that are designed to encompass various operating devices and related activation means, such as, cables and rods, for manipulating the operating devices.

Figure 5:
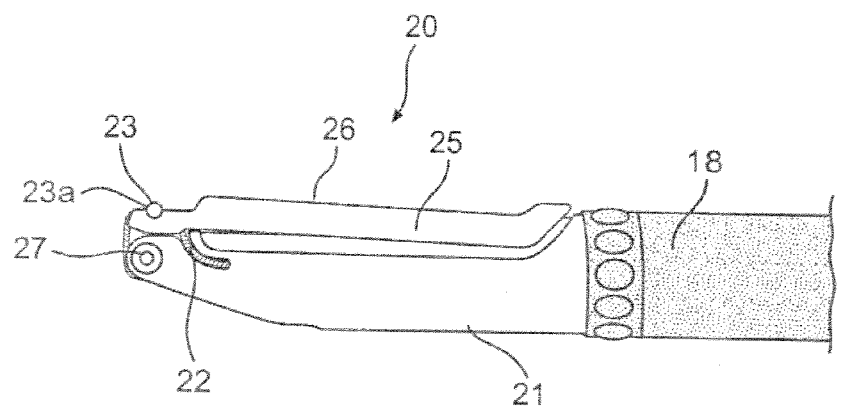
FIGS. 5-7 are side, top, and front views of an A-frame head, respectively, with a folding arm in a closed position, according to an embodiment of the present invention.
Figure 6:
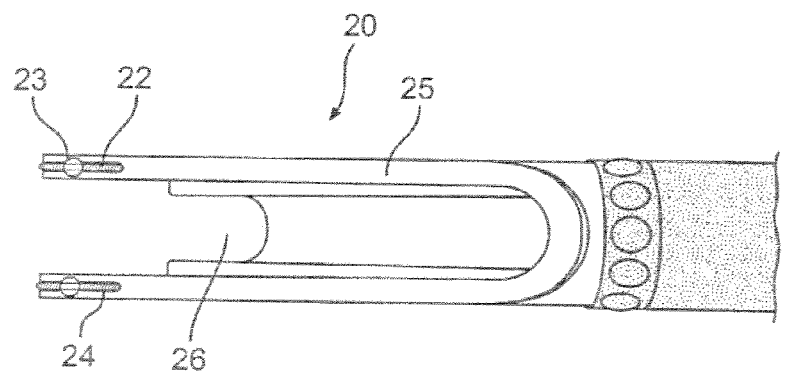
Figure 7:
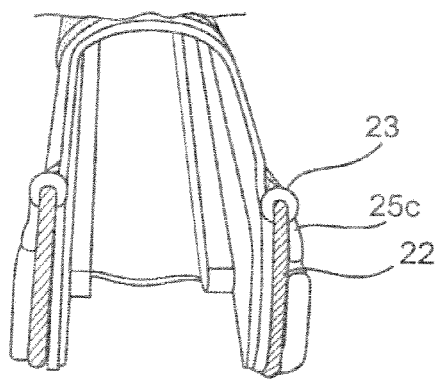

FIGS. 5-7 show side, top, and front views of the A-frame head 20 with a folding arm 25 in a contracted or closed position, according to an embodiment of the present invention. The A-frame head 20 is a relatively short cylindrical tube having a main body 21 and a folding arm 25. The A-frame head 20 may be made of metal, such as stainless steel and titanium, polymers, ceramics, or any combination thereof. The A-frame head 20 has a tapered distal end portion to permit easier passage through a narrow lumen of the body, such as, for example, cricopharyngeal area. The proximal end of the folding arm 25 (i.e., the end-most proximal part when the arm 25 is in the open position) is rotatably coupled to a pivot member 27 disposed in the distal end portion of the main body 21. The pivot member 27 may be a pin or any other suitable mechanism. The outer profile of the folding arm 25 is preferably configured such that, in the closed position, the folding arm 25 is substantially flush with an outer surface of the main body 21, and forms a generally cylindrical outer profile with the main body 21.

FIGS. 8 and 9 show the A-frame head 20 with the folding arm 25 in an extended or open position, according to an embodiment of the present invention. In the open position, the folding arm 25 rotatably extends to receive multiple tissue layers to be folded between the folding arm 25 and the main body 21. The folding arm 25 has a generally U-shaped configuration defining an opening 26 or a slot along its length to permit passage of fastening devices and fastening members, once the multiple tissue layers are folded together and ready to be fastened. On the inner surface of the folding arm 25, a friction-enhancing member, such as, for example, a plurality of teeth 28, are formed to tightly hold the tissue layers during the folding and holding operations. In addition, at least a portion of the A-frame head 20 may be coated with a polymer or elastomer material to provide a softer contact between the tissue and the A-frame head 20 and to enhance the grip of the A-frame head 20 on the tissue.

Figure 11:
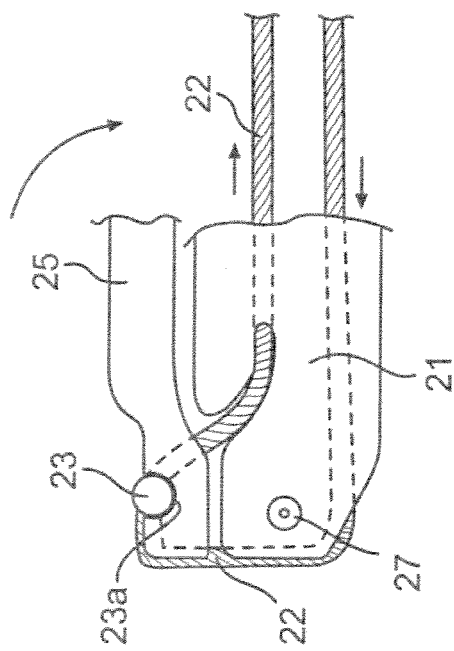
FIGS. 10-11 are schematics illustrating the opening and closing operations of the foldable arm of an A-frame head, according to an embodiment of the present invention.
Figure 10:
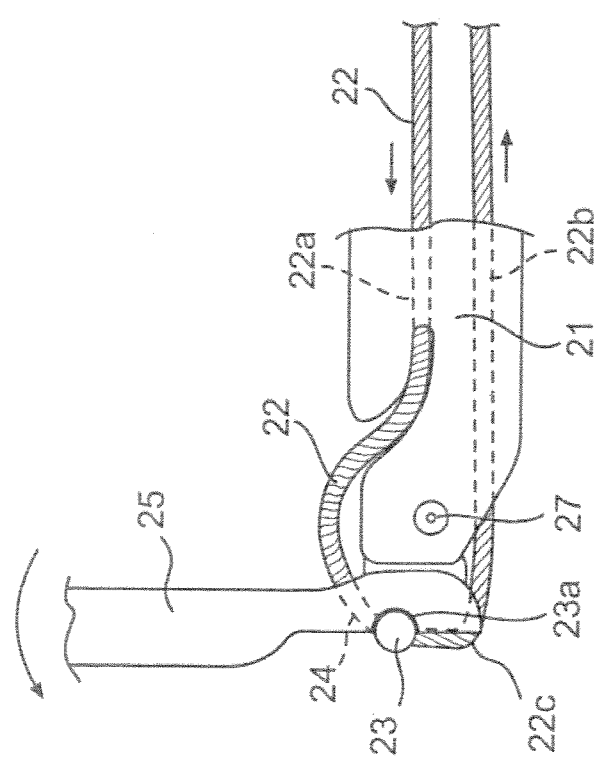

With reference to FIGS. 10 and 11, as well as FIGS. 5-9, the opening and closing operations of the foldable arm 25 of the A-frame head 20 are described herein, according to an embodiment of the present invention. In this embodiment, the opening and closing operations of the folding arm 25 is manipulated by a pair of flexible cables 22 or wires that can be actuated by a suitable mechanism in the A-frame handle 30, which will be described further herein. Each of the pair of cables 22 extends from the A-frame handle 30 to the A-frame head 20 through cable lumens formed in the downtube 15, also to be shown and described further herein. As shown in FIGS. 5-9, each cable 22 passes through one of two cable paths 22a, 22b formed along the length of the each side 21a, 21b of the main body 21. The cable 22 then passes through a cable opening 24 in the folding arm 25, follows around a cable groove 22c formed along the distal end portion of the foldable arm 25, and passes back into the other of the two cable paths 22a, 22b in the main body 21. The cable 22 then extends back to the A-frame handle 30 through the cable lumen of the downtube 15, thereby forming a loop. Preferably, the cable paths 22a, 22b formed in each side of the main body 21 are reinforced lumens, so that the cable can freely slide along the cable paths 22a, 22b.

As can be best seen from FIGS. 10 and 11, an anchoring member, such as, for example, a rigid ball 23, is fixedly attached to the loop cable 22 in the cable groove portion of the folding arm 25. Preferably, a portion of the cable groove 22c forms a ball socket 23a in which the rigid ball 23 is held in place during the opening and closing operation. In operation, by slidably displacing the cable 22 in the directions indicated by the arrows in FIGS. 10 and 11, the folding arm 25 is opened and closed, respectively. More specifically, sliding motion of the cable 22 in the counterclockwise direction exerts a torque on the distal edge portion of the folding arm 25 and causes the folding arm 25 to rotatably open with respect to the pivot member 27. On the other hand, sliding motion of the wire 22 in the clockwise direction exerts an inwardly directed torque on the folding arm 25 and causes the folding arm to close. Although the operation of the foldable arm 25 is described with respect to an exemplary embodiment shown in FIGS. 5-11, it should be understood that any other suitable mechanisms known in the art can be alternatively used.

Figure 12:
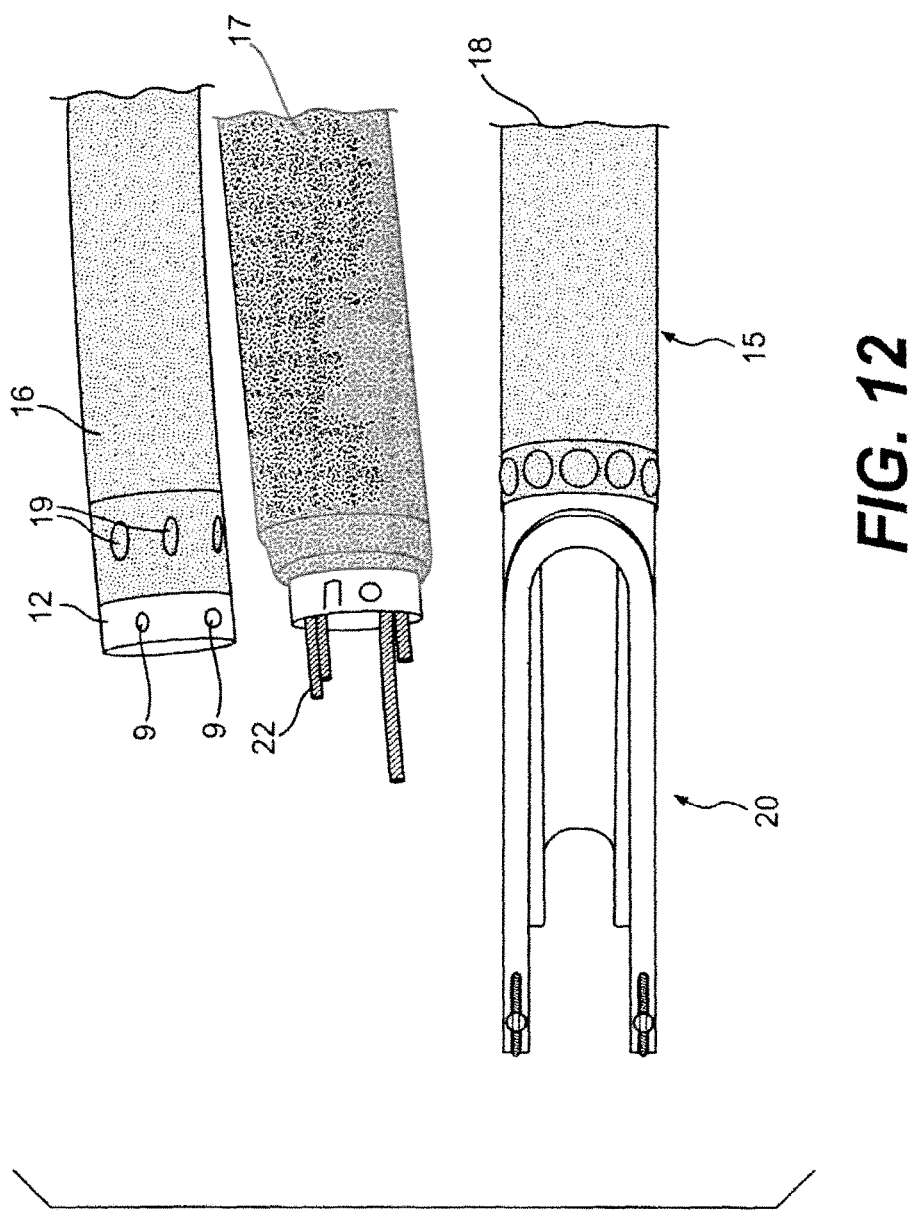
FIG. 12 is perspective views of a downtube, showing different assembly stages, according to an embodiment of the present invention.
Figure 13:
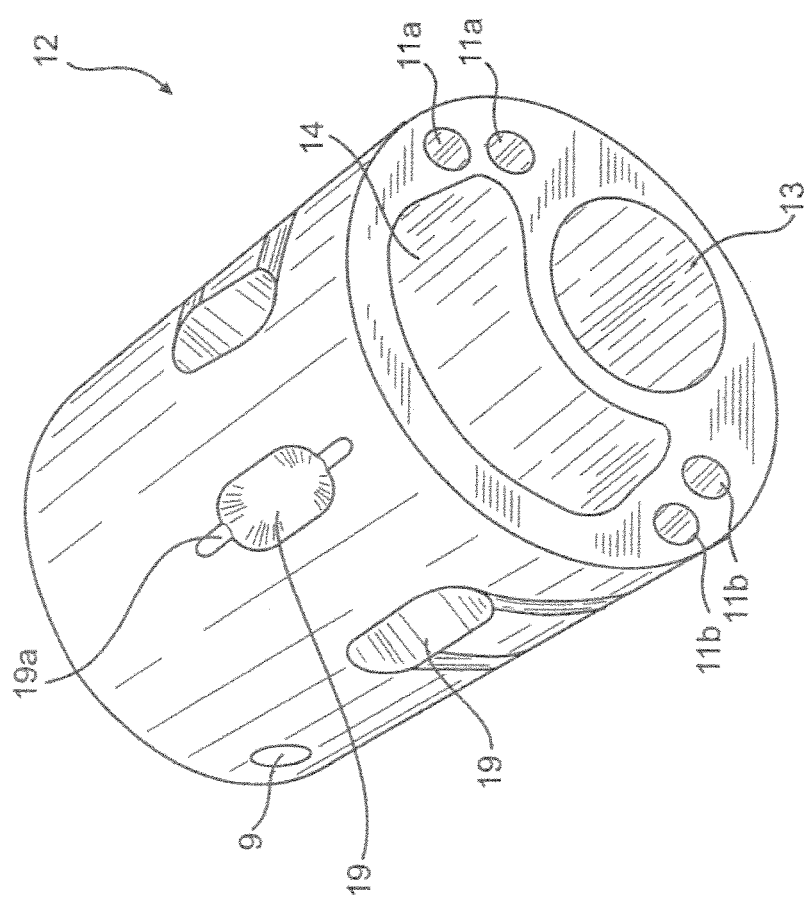
FIG. 13 is a perspective view of a distal adapter, according to an embodiment of the present invention.

FIG. 12 shows various assembly stages of the multi-layered downtube 15, according to an embodiment of the present invention. As shown in the top of the figure, the downtube 15 includes a generally cylindrical polymeric tube 16 reinforced with a flexible polymer braid material. A distal adapter 12 is attached to the distal end of the tube 16 for connection with the A-frame head 20. The attachment between the distal adapter 12 and the tube 16 may be achieved through an interference, friction fit. FIG. 13 shows the distal adapter 12 in detail. The distal adapter 12 is a relatively short rigid piece filled with a polymeric material and has a plurality of lumens 11a, 11b, 13, 14 providing passages for the various operating devices and related cables. In this embodiment, the plurality of lumens include four coil lumens 11a, 11b for the A-frame head operating cables 22, a scope lumen 13 for an endoscope, and a main working channel 14 having an arcuate configuration and providing passages for various operating devices, such as, for example, a grasper and a tissue fastener delivery system. Preferably, at least the main working channel 14 and the scope lumen 13 are reinforced with a polymeric braid material. The outer surface of the distal adapter 12 includes a plurality of openings 19 through which the polymeric filling material makes contact with the inner surface of the cylindrical tube 16 to enhance the adhesion between the cylindrical tube 16 and the distal adapter 12. The outer surface of the distal adapter 12 includes a marking 19a for indicating and aligning the main working channel 14 with the A-frame head 20 during assembly. The distal end of the adapter 12 includes a plurality of holes 9 for connection with the A-frame head 20. In some of the holes, similar to the openings 19 in the proximal end of the adapter 12, the polymeric filling material in the adapter 12 makes contact with the inner surface of the distal end portion of the A-frame head 20 to enhance the adhesion between the A-frame head 20 and the distal adapter 12. On the other hand, some of the holes are used to connect the A-frame head 20 and the distal adapter 12 by screws.

As shown in FIG. 12, once the distal adapter 12 is attached to the distal end of the downtube 15, the cylindrical tube 16 is covered with a layer of polymeric braid material 17. After the A-frame head 20 is connected to the downtube 15 via the distal adapter 20, the downtube 15 is then coated with a polymeric material, such as PVC, as shown in the bottom of FIG. 12.

Figure 14:
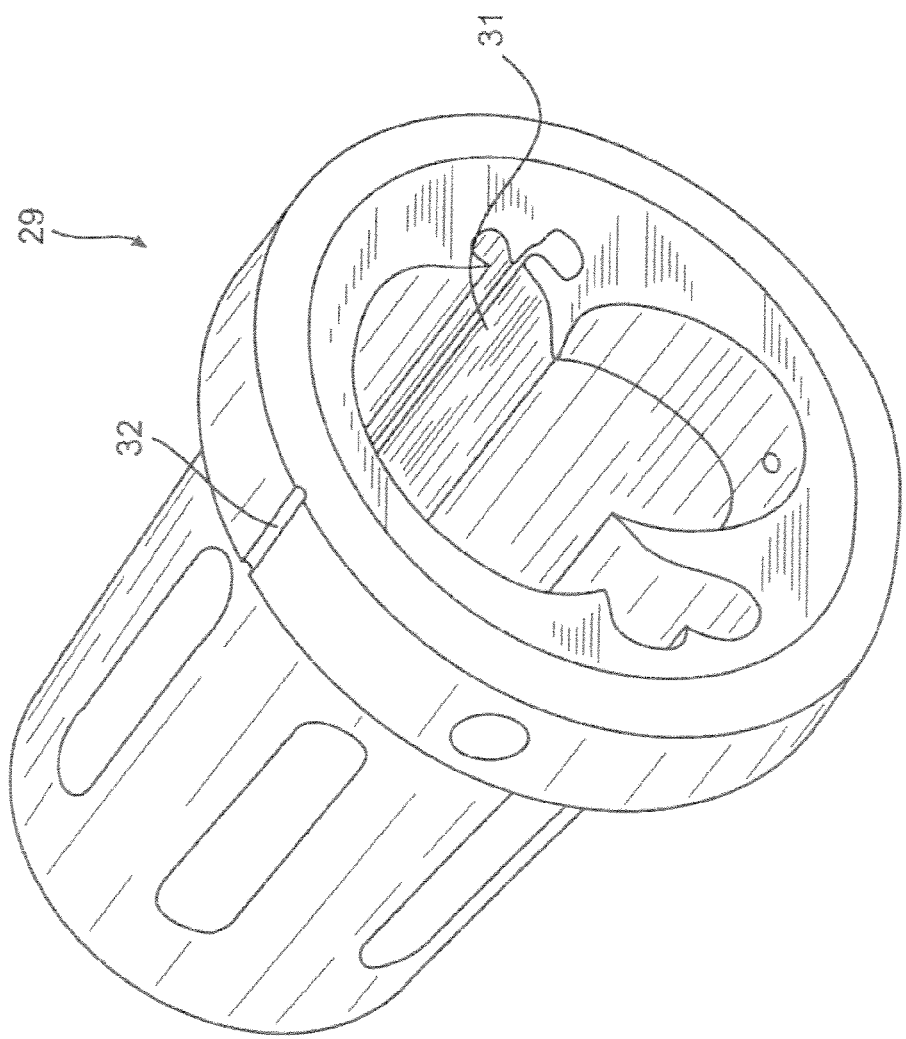
FIG. 14 is a perspective view of a proximal adapter, according to an embodiment of the present invention.

FIG. 14 shows the proximal adapter 29 used to connect the proximal end of the downtube 15 to the A-frame handle 30. The proximal adapter 29 preferably is a relatively short, rigid piece that includes a large lumen 31 providing passages for the various operating devices and related cables. The proximal adapter 29 also includes a marking 32 for indicating and aligning the main working channel portion of the large lumen 31 with the A-frame handle 30 during assembly.

Figure 15:
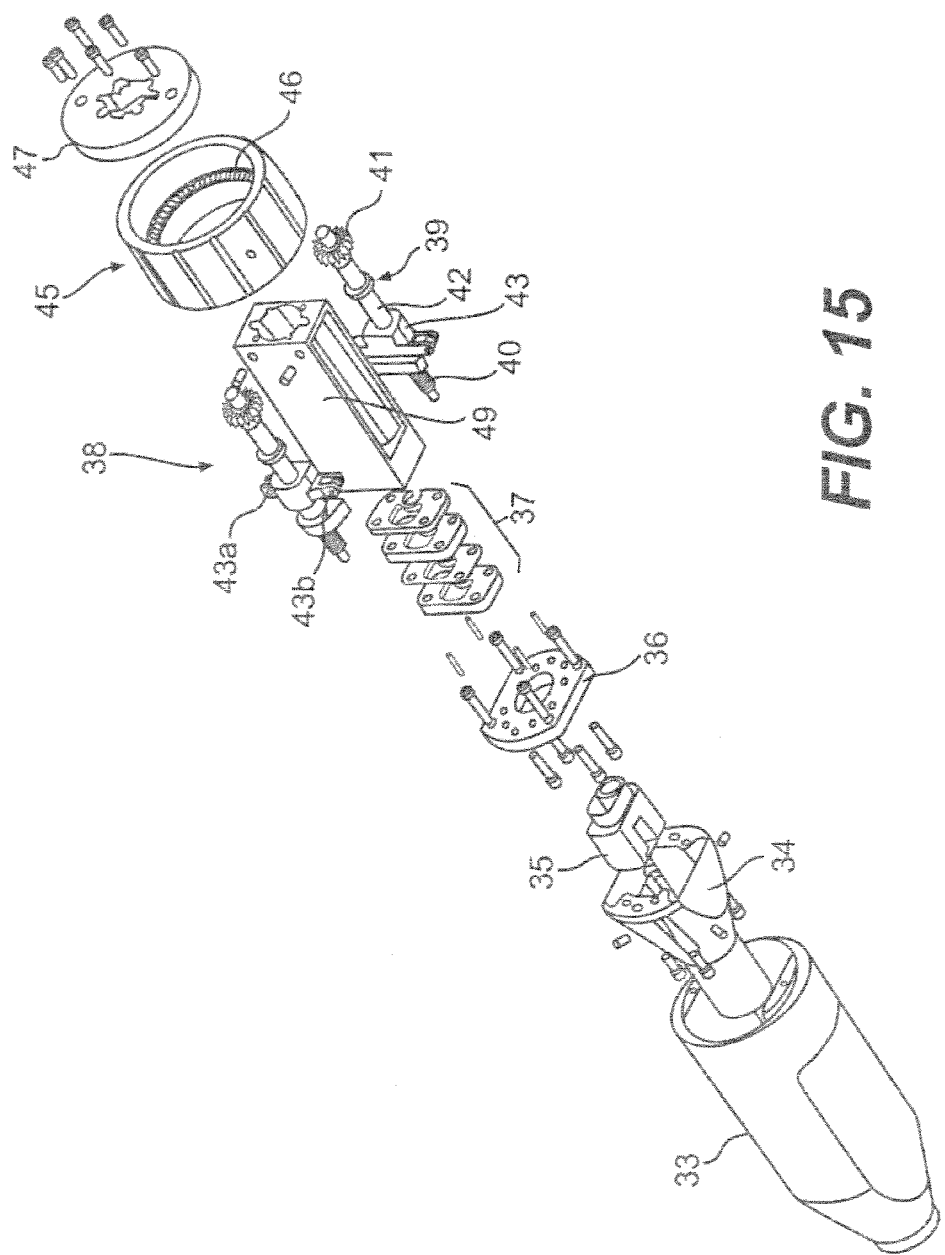
FIG. 15 is an exploded perspective view of an A-frame handle, according to an embodiment of the present invention, showing the components of the A-frame handle.
Figure 16:
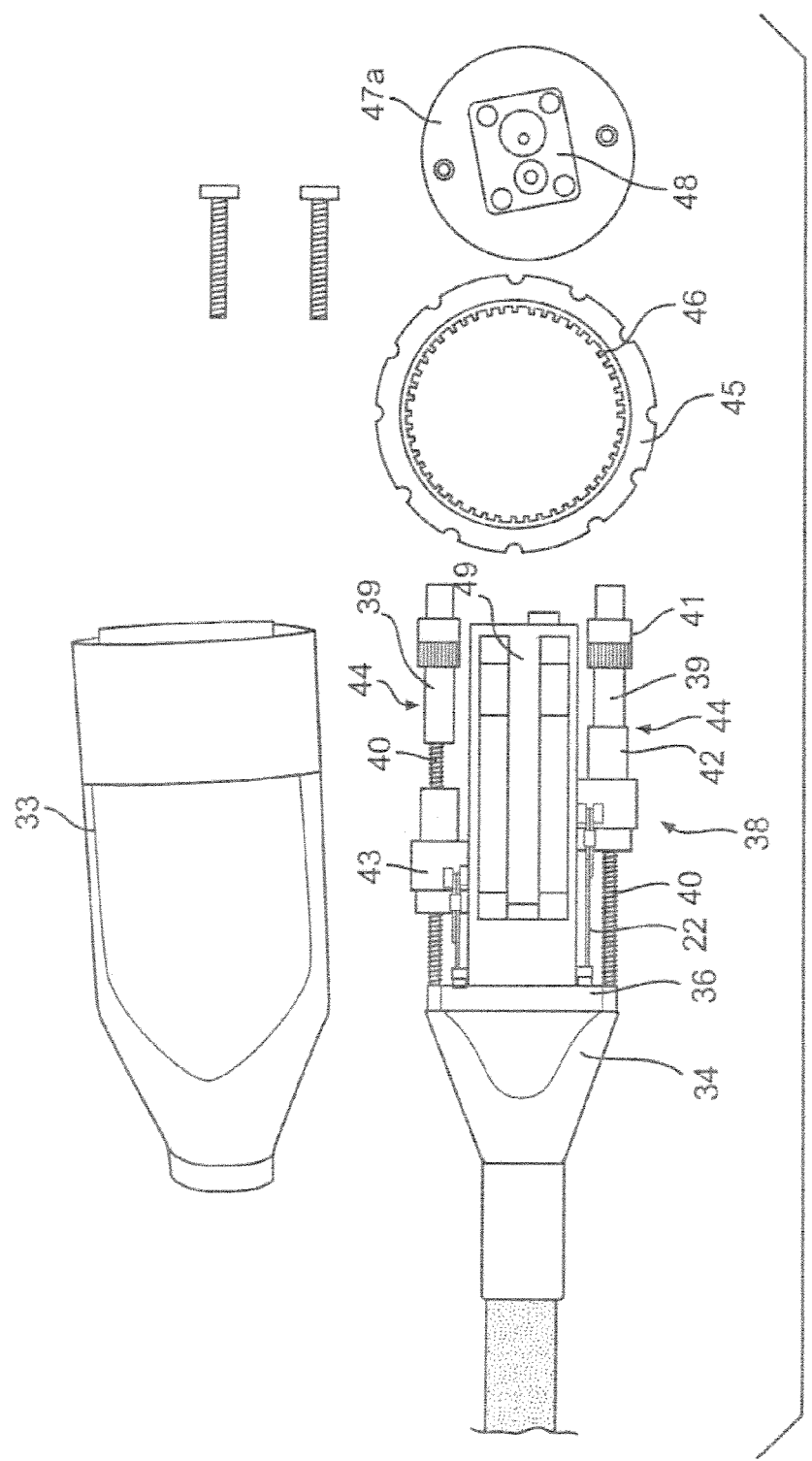
FIG. 16 is a side view of an A-frame handle, according to another embodiment of the present invention, with portions removed to expose components.

FIG. 15 is an exploded view, showing individual components of the A-frame handle 30, according to an embodiment of the present invention. The A-frame handle 30 includes a handle cover 33, a front transition piece 34 having a bearing plate 36 and a funnel 35, a plurality of sealing members 37, an actuation device 38, a handle knob 45 with an actuation gear 46 on its inside surface, and a backing plate 47. FIG. 15 also shows a plurality of pins, screws, or other like means for attaching these various components together. FIG. 16 shows an A-frame handle 30, according to another embodiment of the present invention. This embodiment is substantially identical to the embodiment shown in FIG. 15 except that: the funnel 35 and the plurality of sealing members 37 are replaced with a sealing plate 48 on a backing plate 47a and sealed channels 52, 53, which will be described further herein.

The handle cover 33 is preferably is one-piece polymer and encompasses all of the components of the handle 30, except the knob 45. The front transition piece 34 snaps into the cover 33 in the most distal portion of cover 33 and functions as a spacer for mechanical connection between the A-frame head 20 and the handle. The funnel 35 is configured to fit inside the transition piece 34 and provides means for sealing the device from the gases and fluids of the stomach. The bearing plate 36 covers the transition piece 36. The plurality of sealing members 37 provides additional and redundant sealing means for the gases and fluids of the stomach. Once all components except the knob 45 are assembled into the cover 33, the cover 33 is inserted into the distal end of the knob 45 and the backing plate 47 is fixedly attached to the proximal end face of the cover 33 through the knob 45.

Figure 17:
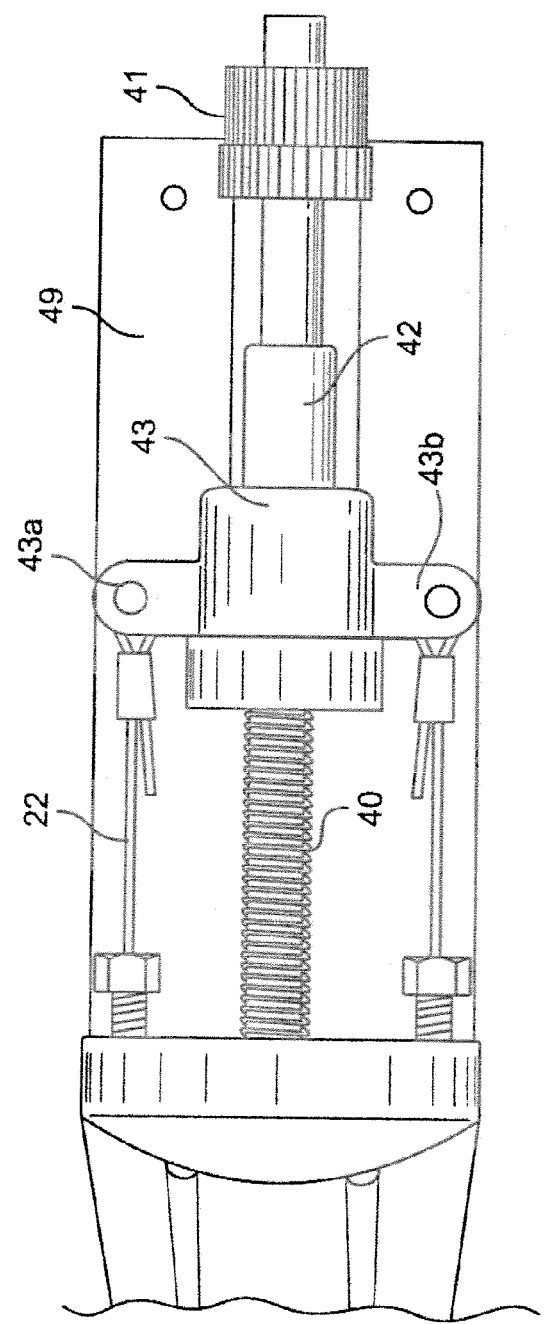
FIG. 17 is a partial top view of an A-frame handle, with portions removed to show certain components.

As shown in FIGS. 16 and 17, the actuation device 38 includes a pair of clamp drives 44 disposed on opposite sides of a main body 49. Each of the clamp drives 44 includes a gear shaft 39 having a threaded portion 40 on its distal portion, and a gear 41 on its proximal portion for engagement with the actuation gear 46 of the handle knob 45. The threaded portion 40 on the gear shaft 39 is inserted into a threaded cylindrical follower 42, and a yoke 43 having a pair of pinions 43a, 43b is fixedly attached on the outer surface of the follower 42, such that the yoke 43 can float axially along the threaded portion 40 of the gear shaft 39.

As shown in FIG. 17, the A-frame head operating cables 22 are connected to the pair of pinions 43a, 43b of the yoke 43. One end of each cable 22 is connected to each of the pinions of the same yoke 43 shown in FIG. 17. For example, the two cables 22 connected to the top yoke 43 are the cables 22 passing through the upper cable path 22a in each side of the A-frame head 20, while the two cables 22 connected to the bottom yoke 43 are the cables 22 passing through the lower cable path 22b. Thus, in operation, when the handle knob 45 is rotated, the actuation gear 46 causes the gear shafts 39 to rotate in the same direction. Since the clamp drives 44 are disposed on opposite side of each other, the rotation of the handle knob 45 causes each of the yokes 43 to move in opposite directions to each other. The relative movement of the top and bottom yokes 43 drives the opening and closing operations of the folding arm 25 of the A-frame head 20.

Figure 18:
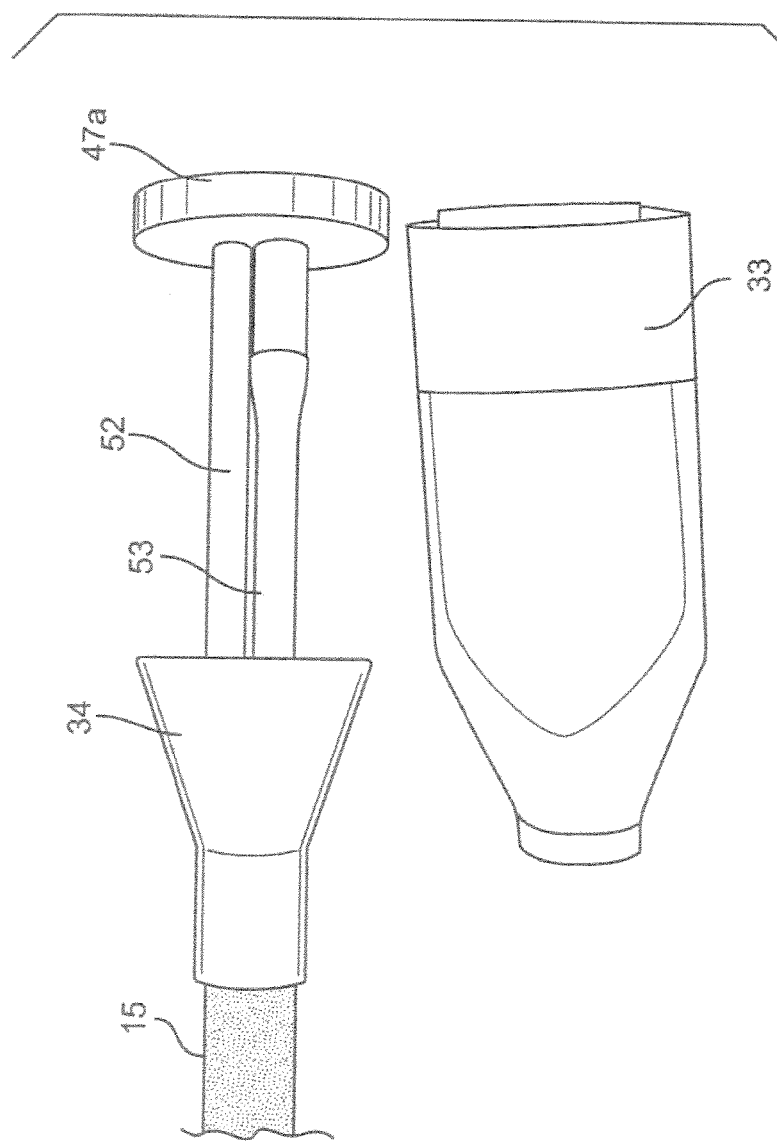
FIGS. 18-19 are side and end views of an A-frame handle, shown in FIG. 16, without the actuation device in place.
Figure 19:
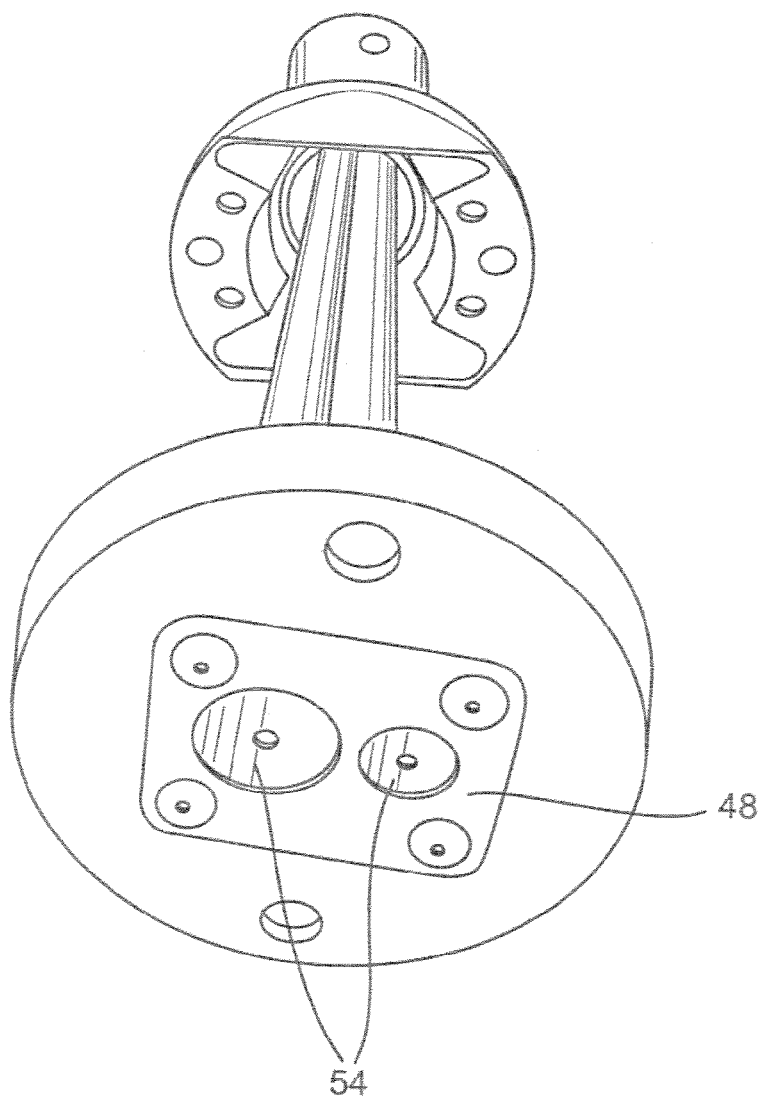

FIGS. 18 and 19 show the A-frame handle 30 without the actuation device 38 in place. The A-frame handle 30 includes a channel 52 for an endoscope and a channel 53 for other various operating devices. These channels 52, 53 are accommodated in the main body 49 of the actuation device 38. Once the main body 49 containing the cable actuation device is installed, the backing plate 47a having sealing members 54 for the channels 52, 53 are attached at the proximal ends of the channels. The sealing members 54 may extend into channels 52, 53 to such a depth as to obviate the need for the plurality of sealing members 37 shown in FIG. 15.

Protection Device

Figure 20:
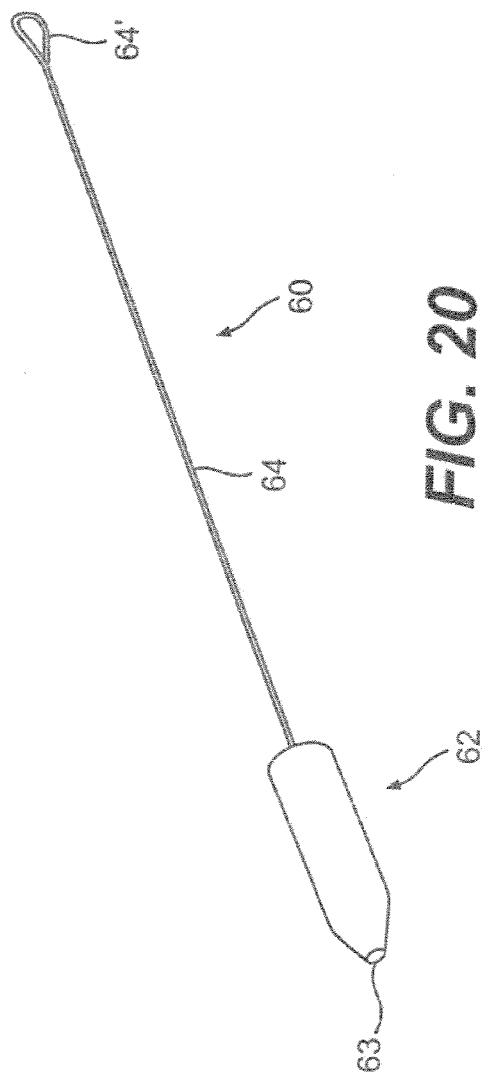
FIG. 20 is a perspective view of a protection device, according to an embodiment of the present invention.

FIG. 20 shows a protection device 60, according to an embodiment of the present invention. The protection device 60 is used to protect the esophageal wall 4 from possible damage during insertion of the A-frame device 10 into the esophagus 3 by covering the distal end portion of the A-frame device 10. The device 60 includes a protective sleeve 62 and a handle 64 having a length sufficient to extend outside of a body. The sleeve 62 is generally cylindrical in shape with tapered distal end and is made of materials having sufficient strength to resist tearing from sharp edges or protrusions from the endoscopic instrument it covers. The sleeve 62 also has sufficient flexibility and deformability, so that it can be pulled back through the working channel of the A-frame device 10 once the A-frame device 10 is in position in the stomach.

Figure 21:
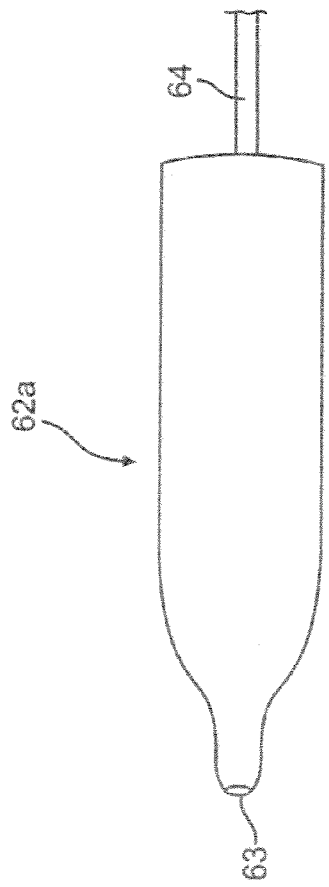
FIG. 21 is a side view of a protection device, according to another embodiment of the present invention.

Preferably, the sleeve 62 is made of a polymer mesh (e.g., tetrahydrophurane) reinforced with polyurethane coating. However, any other suitable materials known in the art, including mylar, nylon, PET, polyethylene, or vinyl, can also be utilized. In addition, the surface of sleeve 62 can be coated with a hydrogel or any other lubricating material known in the art to allow easier passage through the esophagus 3 or other body lumens. The sheath 62 also has an opening 63 on its distal end to permit passage of an endoscope for viewing. The sleeve 62 may also be made of a translucent material for the endoscope to view and position the A-frame device 10 more precisely. The handle 64 has sufficient flexibility to pass through the esophagus. The handle 64 has a proximal holder 64', both of which have a sufficient, small diameter to insert within the working channel of the A-frame device 10. Preferably, the protection device 60 is back-loaded into the A-frame device 10, i.e., loaded into the distal end of the A-frame device 10. Handle 64 has FIG. 21 shows an alternative embodiment of a sleeve 62a. The sleeve 62a has a tapered distal portion slightly longer than the one shown in FIG. 20, and may be made of a more flexible thin membrane material. Typical thickness of a sleeve 62, 62a may range from 0.005 inch to 0.010 inch with a nominal thickness of 0.010 inch.

Figure 22A:
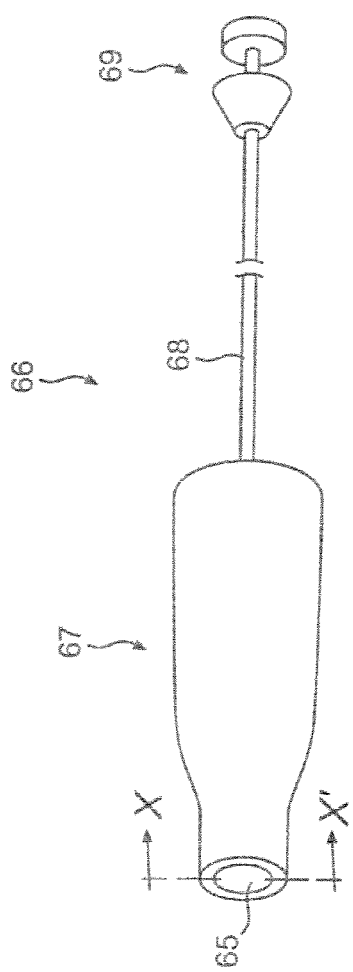
FIG. 22A is a perspective view of a protection device, according to still another embodiment of the present invention.
Figure 22B:
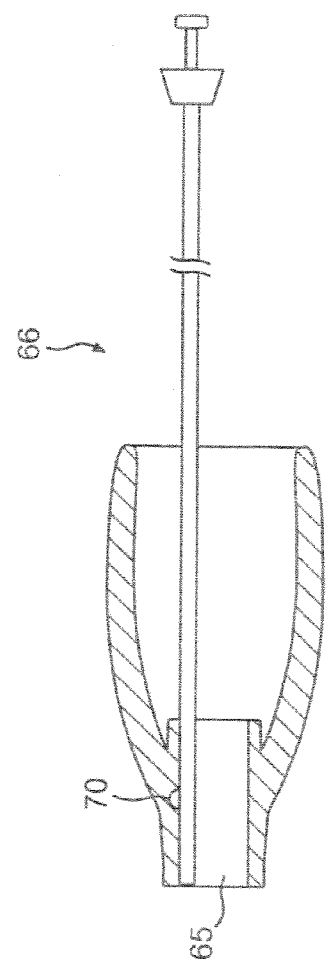
FIG. 22B is a cross-sectional view of the protection device shown in FIG. 22B along the X-X' plane of FIG. 22B.

FIGS. 22A and 22B show a protection device 66, according to still another embodiment of the present invention. The protection device 66 includes a generally hollow, cylindrical, inflatable balloon 67 with tapered distal end, and a fluid-supplying member 69 disposed at its proximal end. The fluid-supplying member 69 may also include a connector, such as, for example, a luer-lock type connector, for connecting to a source of air or other bio-compatible fluid (e.g., saline solution) to fill the balloon 67. Prior to insertion of the A-frame device 10, the fluid-supplying member 69 supplies the bio-compatible fluid to the balloon 67 through a fluid-supply tube 68. A distal portion of the balloon 67 has a port 70 in fluid communication with the tube 68 for receiving air and inflating the balloon 67. During the insertion, the inflated balloon 67 predilates the esophagus before the A-frame head 20 makes contact with the esophageal tissue and thereby protects the esophageal tissue from potential damages caused by the contact between the A-frame head 20 and the tissue. The cylindrical opening 65 of the balloon 67 provides a passage for an endoscope for viewing. Once the balloon 67 is fully inflated, the balloon 67 seals the gap between the balloon 67 and the endoscope during the insertion.

The fluid-supply tube 68 may also be used as a handle for removing the protection device 66. After the balloon 67 is deflated, the tube 68 is pulled to withdraw the balloon 67. The balloon 67 having sufficient flexibility becomes inverted and fit through the working channel of the A-frame device 10. Other suitable devices, such as a stylet or a flexible cable, can be used with, or in place of, the fluid-supply tube 68 for the insertion/removal operations.

FIGS. 23A and 23B show a protection device 78, according to still another embodiment of the present invention.

Similar to the protection device 66 shown in FIGS. 22A-22B, the device 78 includes a generally hollow, cylindrical, inflatable balloon 75 with taped distal end portion 74. In this embodiment, the distal end portion 74 of the balloon 75 has a thicker inflated portion 76 than the rest of the balloon 75, providing a bumper in front of the A-frame head 20. The inside surface of the distal end portion 74 includes a fluid-supply port 77 in fluid communication with a fluid-supply tube 68 for receiving air and inflating the balloon 75. When the balloon 75 is inflated and an endoscope is inserted through the opening 65, the balloon 75 can be provided with means for sealing the gap between the balloon 75 and the endoscope during the insertion.

Other various embodiments of a protection device, such as the embodiments described in the commonly assigned U.S. application Ser. No. 09/920,809 of Yem Chin, filed on Aug. 3, 2001, the disclosure of which is hereby incorporated by reference, may alternatively be utilized.

Invagination Device

Figure 24:
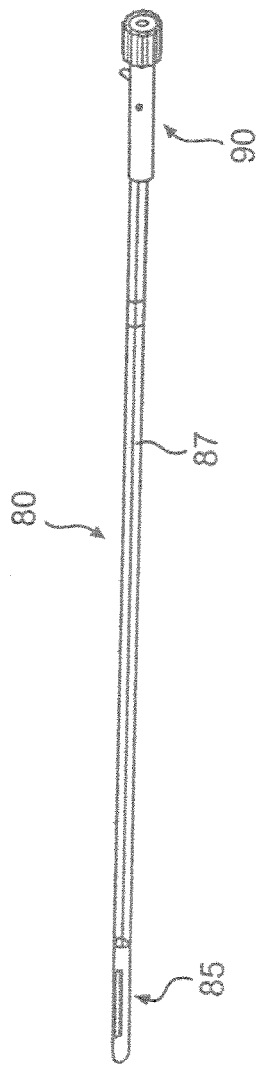
FIG. 24 is a perspective view of a suction grasper, according to an embodiment of the present invention.
Figure 25:
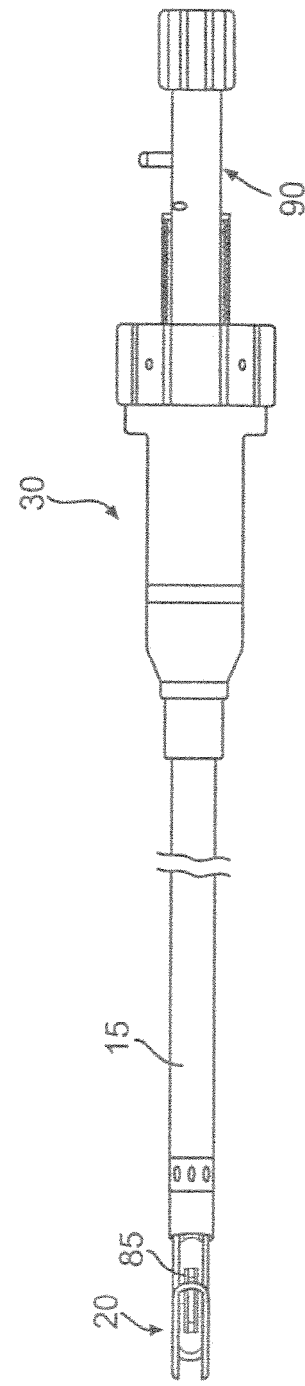
FIG. 25 is a perspective view of an A-frame device, shown in FIG. 4, with the suction grasper shown in FIG. 24.

FIG. 24 shows an invagination device, according to an embodiment of the present invention. The invagination device shown in the figure is a suction grasper 80 that uses an air suction mechanism to grasp tissue. The grasper 80 includes a grasper head 85, a coil lumen 87, and a grasper handle 90, as its main components. The suction grasper 80 has an outer diameter slightly less than the inner diameter of the working channel of the A-frame device 10, so that the grasper 80 can be inserted into the working channel of the A-frame device 10, as shown in FIG. 25.

Figure 26:
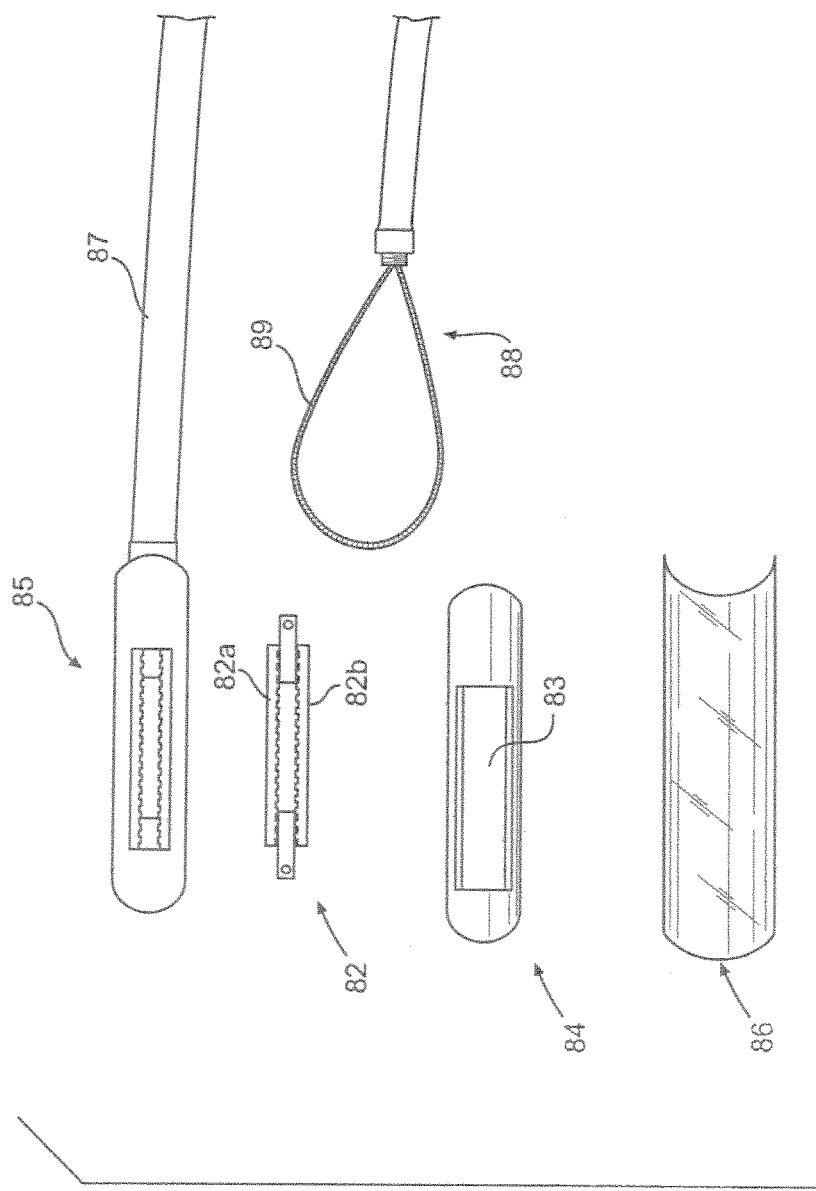

FIGS. 26 and 27 are top and bottom views of the grasper head 85 showing various components of the grasper head 85. The top portion of each figure shows the grasper head 85 in the assembled configuration, and the remaining portions of each figure show the separate components. The grasper head 85 can be made of metal, such as stainless steel or titanium, polymers, ceramics, or any other combination thereof. In addition, at least a portion of the grasper head 85 may be coated with a polymer or elastomer material to provide a softer contact between the tissue and the grasper head 85 and to enhance the grip of the grasper head on the tissue.

The grasper head 85 includes a head 84, a jaw assembly 82, a translucent concave insert 86 made of a polymer or glass, and a jaw operating device 88. The head 84 has an opening 83 through which the tissue is grasped by suction. FIGS. 27A-27D schematically illustrate various assembly connection stages of the jaw assembly for operation. The jaw assembly 82 includes a pair of jaws 82a, 82b welded to a flexible spring set 82c that is biased open. The spring set 82c has an opening 82d, 82e on each end and is fixed to the grasper head 84 with a suitable fixing means, such as screws. The jaw operating device 88 includes a loop of operating cable 89. Each of the jaws 82a, 82b has a groove 82f, 82g milled in its side portion, and the operating cable 89 passes between the spring set 82c and the groove 82f, 82g, as shown in FIG. 27D. During assembly, one end of the cable 89 is passed, in order, through the proximal opening 82d of the spring set 82c, through the groove 82f, 82g of one of the jaws 82a, 82b, through the distal opening 82e of the spring set 82c, through the groove 82f, 82g of the other of the jaws 82a, 82b, and finally through the proximal opening 82e. Preferably, the operating cable 89 is twisted at its distal end after passing through the distal opening 82d to form a small loop 89a at its distal end, so that the cable 89 is connected to the opening 82d with the crossed cable, as shown in FIG. 27C. The proximal opening is connected to the cable 89 in similar manner.

In operation, pulling the loop of operating cable 89 (by handle 90 as described below) causes the flexible spring set 82c for deform into a U-shaped configuration, thereby causing the pair of jaws 82a, 82b close. The pair of jaws 82a, 82b are disposed in the close vicinity of the opening 83 to hold the tissue more tightly once suction has been applied. The concave insert 86 covers the back side of the grasper head 84 to form a suitable vacuum inside the suction grasper head 85. Since the concave insert 86 is translucent, so that the process of grasping and holding of the tissue can be readily observed from an endoscope.

Figure 28:
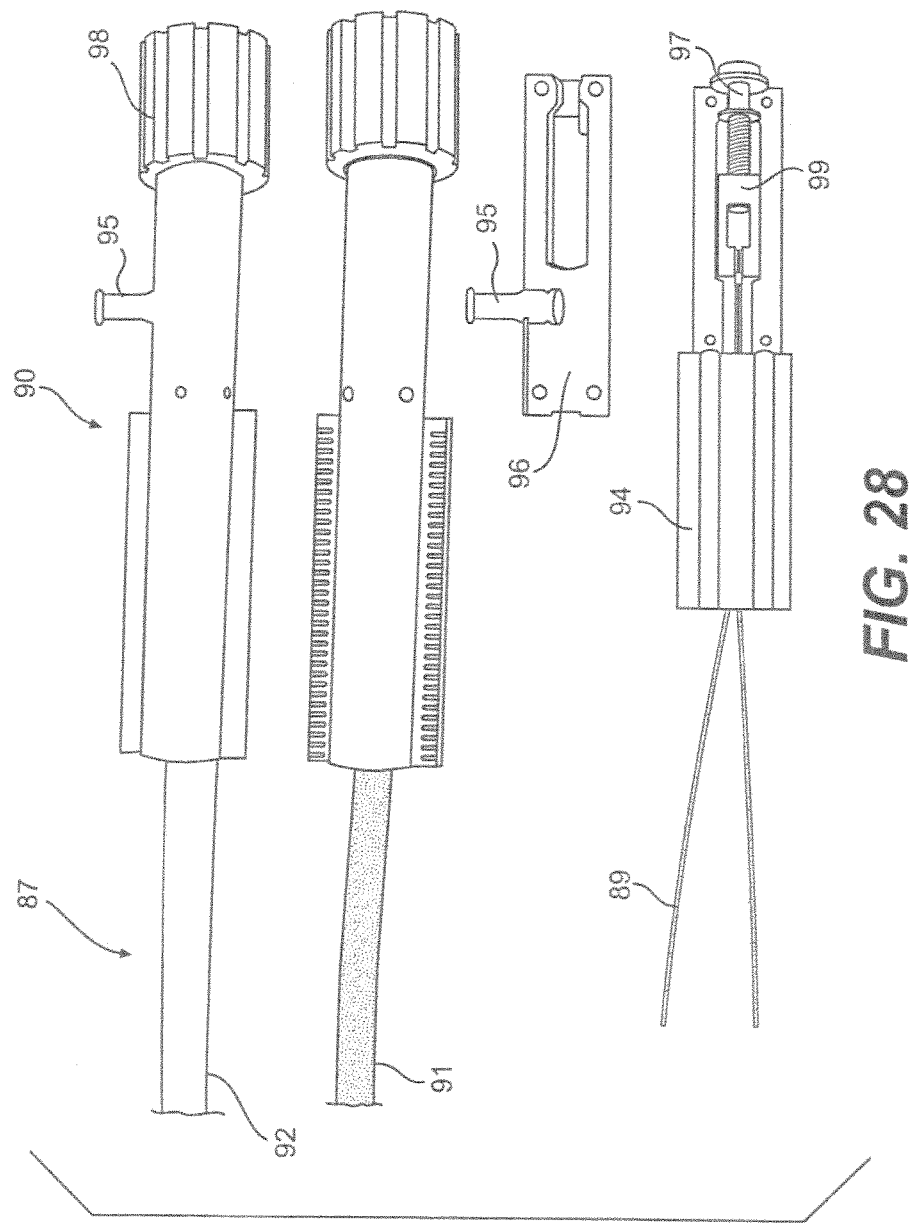
FIG. 28 is various views of a grasper handle, according to an embodiment of the present invention.
Figure 29:
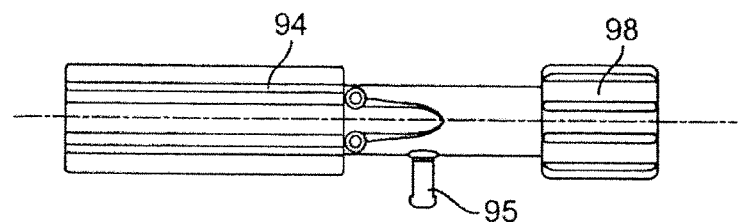
FIG. 29 is a side view of the grasper handle shown in FIG. 28.
Figure 30:
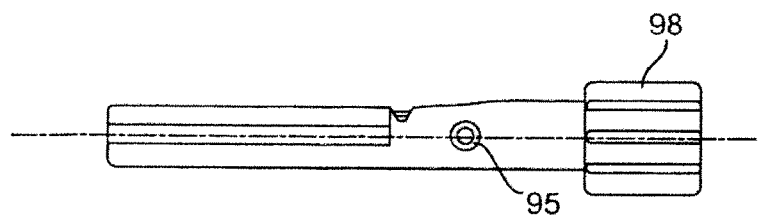
FIG. 30 is another side view of the grasper handle shown in FIG. 28.
Figure 31:
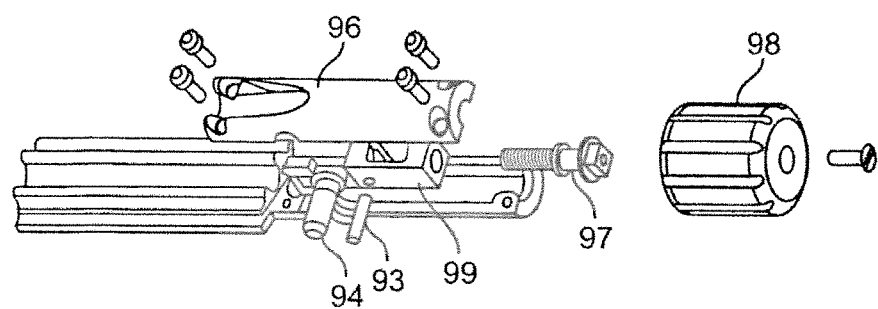
FIG. 31 is an exploded perspective view of the grasper handle shown in FIG. 28, showing various components of the grasper handle.

FIGS. 28 through 31 show the grasper handle 90 that connects to the grasper shaft 87 to operate the grasper head 85. As shown in FIG. 28, the grasper shaft 87 is a single or multiple wound coil 91 covered with a heat shrink material 92. The grasper shaft 87 is rigid enough to push the grasped esophageal tissue into the stomach, yet flexible enough to traverse tortuous anatomy of a body. Alternatively, the grasper shaft 87 can be any device known in the catheter art, including, but not limited to, single or multiple extrusions, braid, or coil reinforcements and hypotubes.

The grasper handle 90 includes a base 94, a cover 96, and a jaw knob 98. The jaw knob 98 is mechanically coupled to a threaded shaft 97. A follower 99 is inserted into the threaded shaft 97 so that, when the threaded shaft 97 is rotated, the follower 99 can move axially along the threaded portion of the threaded shaft 97. The loop of operating cable 89 is crimped on the follower 99 by a pin 93 (see FIG. 31). The cover 96 includes a tube fitting 95 through which a vacuum suction is provided, and the base 94 has a hollow bore in communication with the coil lumen 87. Various sealing members, such as, for example, O-rings, rubber seals, etc., are used to seal off the vacuum path from the tube fitting 95 to the grasper head 85.

In operation, a source of vacuum (not shown) is connected to the tube fitting 95 to create a desired amount suction in the grasper head 85, shown in FIGS. 26 and 27. The tissue is thereby sucked and held in the opening 83 of the grasper head 85. Once the tissue is properly held in the opening 83, the jaw knob 98 is rotated to cause rotation of the threaded shaft 97, which in turn moves the follower 99 in the direction away from the grasper head 85. The movement of the follower 99 then pulls the cables 89 and causes the jaws 82a, 82b to close and firmly grasp the tissue held in the opening 83 by suction.

In alternative embodiments, other invagination devices having various tissue securing means, such as, for example, clamps, forceps, hooks, suction cups or tubes, can be utilized.

Fastener Delivery System

With reference to FIGS. 32 through 36, a fastener delivery system, according to an embodiment of the present invention, is described herein. The delivery system 100 includes a delivery guide 101, a delivery needle 120, and a pusher 125 as its main components. The delivery system 100 is used to deliver and deploy a tissue fastener to the tissue layers to be fastened together.

Figure 34:
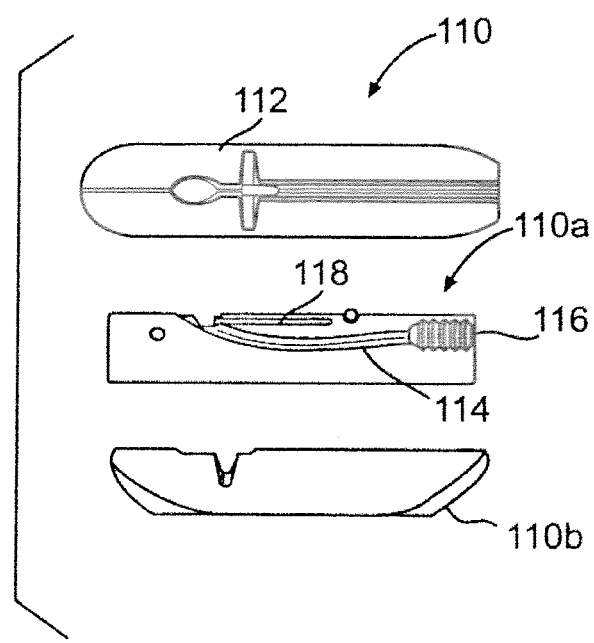
FIG. 34 is detailed views of a two-piece head of the fastener delivery system shown in FIG. 32.

The delivery guide 101 includes a driver head 110 connected to a conduit 105 via a threaded transition piece 115, and a proximal handle 130. FIG. 34 shows the construction of the driver head 110, according to an embodiment of the present invention. In this embodiment, the head 110 is two interconnected pieces, shown in the bottom two figures in FIG. 34. The top figure of FIG. 34 is the assembled head 110. The 110 can be made of metal, such as stainless steel or titanium, polymers, ceramics, or any other combination thereof. In addition, at least a portion of the head 110 may be coated with a polymer or elastomer material to provide a softer contact with tissue.

Figure 35:
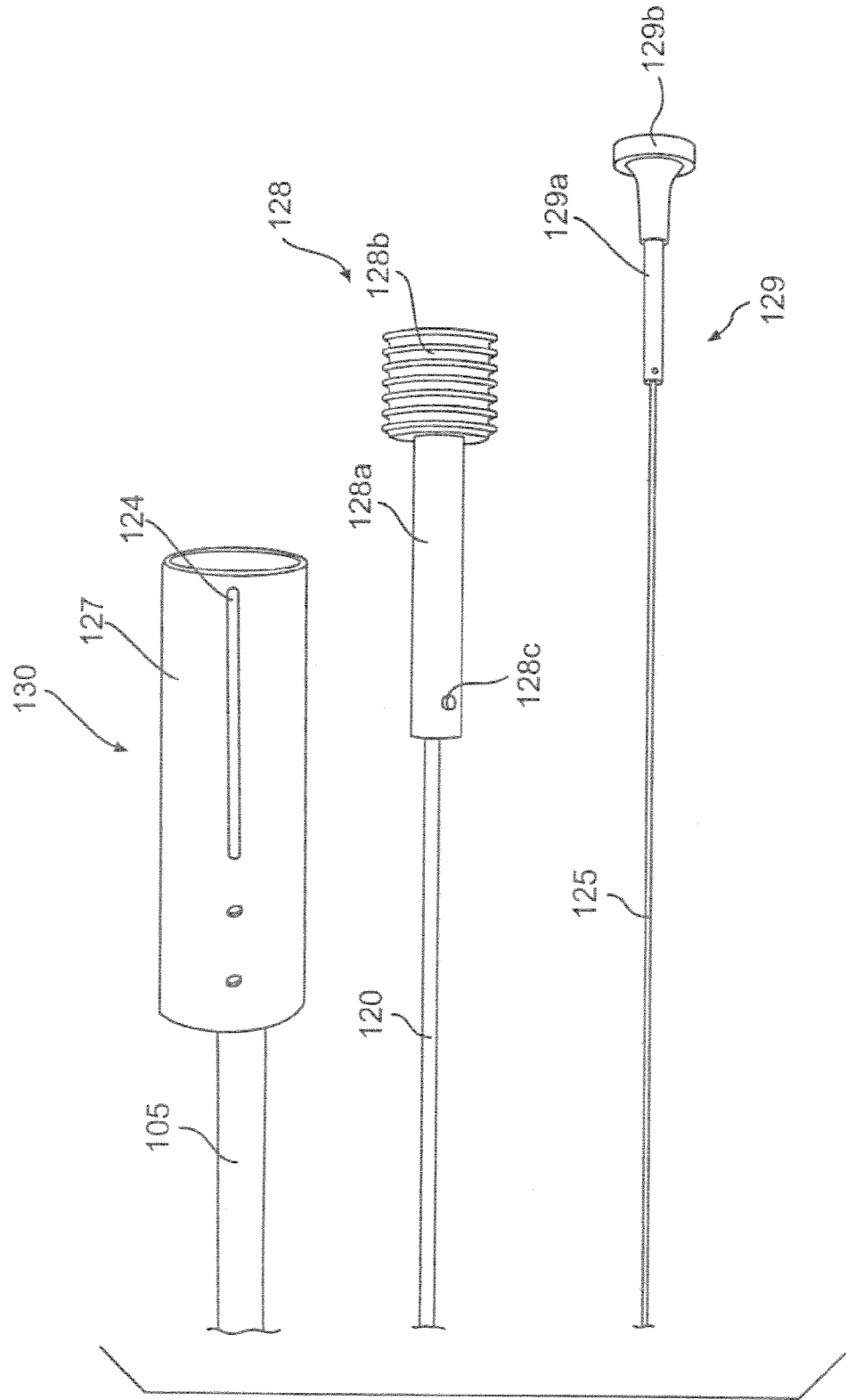
FIG. 35 is side views of a main body, a needle driver, and a pusher driver of a delivery system handle, according to an embodiment of the present invention.
Figure 36:
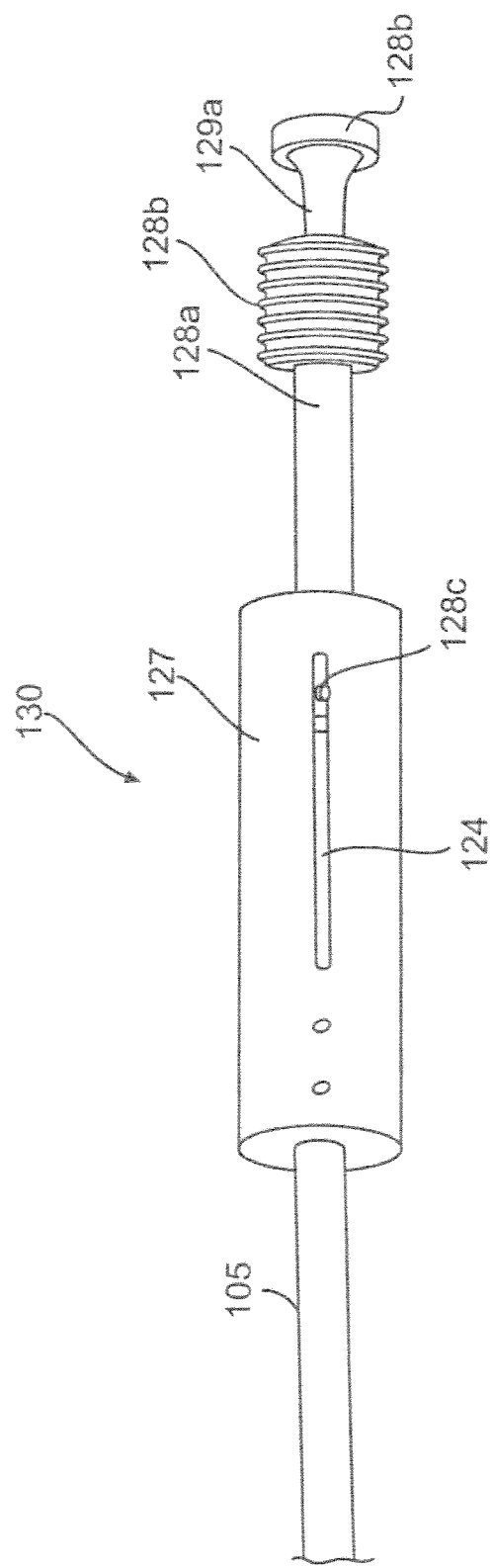
FIG. 36 is a side view of a delivery system handle, according to an embodiment of the present invention.

The head 110 includes a fastener seat 112 formed on its top surface. As will be described further herein, a proximal member 201a, 221, 231, 241 of a fastener 200, 210, 220, 230, 240 is placed in the fastener seat 112 for deployment. The shape of the fastener seat 112 may vary depending on the type and shape of the fastener in use. As shown in the middle of FIG. 34, the head 110 includes a threaded portion 116 for coupling with the transition piece 115 of the conduit 105, and an internal groove 114 with a desired predetermined deflection angle for passage of the needle 120. Preferably, the head 110 may include an internal slot 118 for placing a cutting member 212 to cut excess connecting member material after the fastener is deployed in place, as will be described further herein. Alternatively, the head 110 or the needle 120 may include a cutting member to cut the excess connecting member material. The conduit 105 may be a coiled lumen covered with a heat shrink material. As shown in FIG. 35, the proximal end of the conduit 105 is connected to a drive handle 127. The drive handle 127 may include an elongated slot 124 to limit axial and rotational motion of the needle 120 slidably inserted inside the lumen of the delivery guide 101, as will be described further herein.

Figure 32:
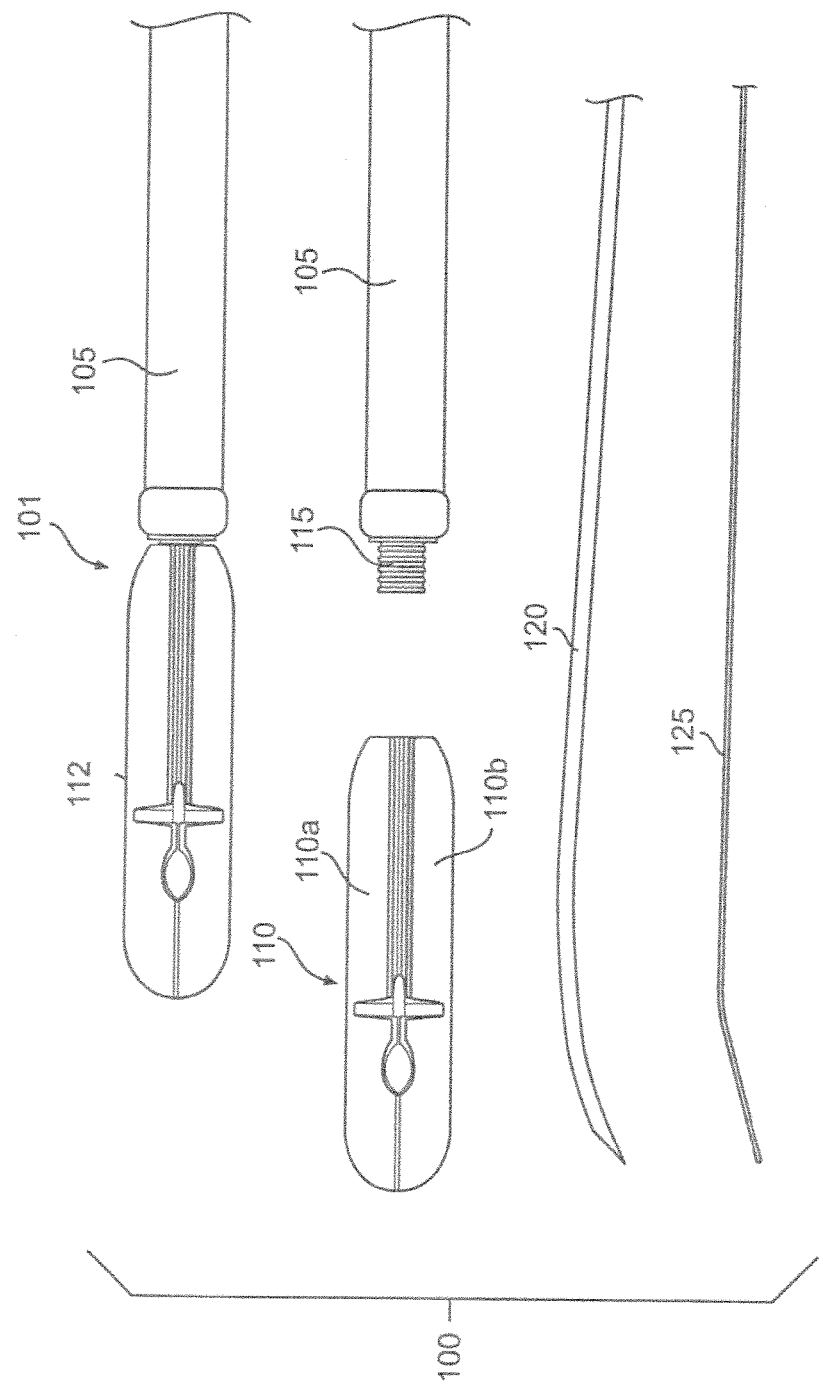
FIG. 32 is perspective views of a fastener delivery system showing various components of the system, according to an embodiment of the present invention.
Figure 33:
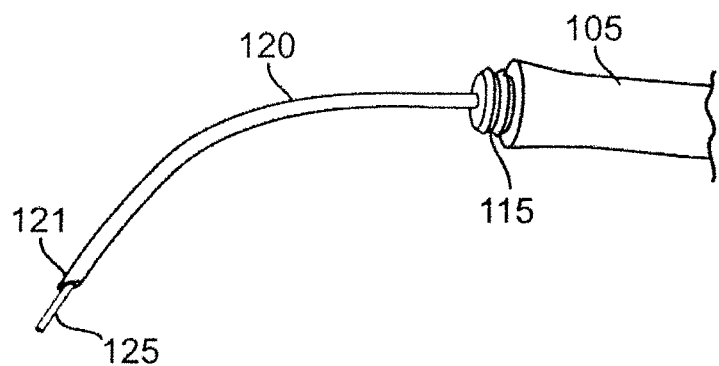
FIG. 33 is a side view of a needle and a pusher, according to an embodiment of the present invention.

Bottom two figures of FIG. 32 show a delivery needle 120 and a delivery pusher 125, according to an embodiment of the present invention. As shown in FIG. 33, the needle 120 has a pre-curved distal end portion and a sharp beveled distal end 121 for perforating the folded tissue layers during deployment of a tissue fastener. The delivery needle 120 is a hollow conduit that has an outer diameter smaller than the inner diameter of the delivery guide lumen, and is thereby configured to slide inside the lumen relative to the delivery guide 101. The pusher 125 is preferably flexible cable that has an outer diameter smaller than the inner diameter of the delivery needle 120, so that the pusher 125 can be slidably inserted into the needle 120. FIG. 33 show the distal portion of the needle 120 and the pusher 125, according to an embodiment of the present invention.

Bottom two figures of FIG. 35 show a needle driver 128 for the delivery needle 120 and a pusher driver 129 for the delivery pusher 125, according to an embodiment of the invention. The needle driver 128 is a hollow tube that includes a generally cylindrical distal portion 128a having an outer diameter slightly less than the inner diameter of the drive handle 127, and a generally cylindrical distal portion 128b having an outer diameter greater than the inner diameter of the drive handle 127. The distal portion 128b thus limits the movement of the needle 120 once inserted within the lumen of the drive guide 101 and prevents the needle 120 from falling into the lumen. The needle driver 128 may also include a guide member 128c protruding transversely with respect to the outer surface of the needle driver 128. The guide member 128c is guided within the elongated slot 124 formed in the drive handle 127 to limit the axial and rotational motion of the needle driver 128.

The pusher driver 129 may also include a distal portion 129a having an outer diameter slightly less than the inner diameter of the needle driver 128, and a distal portion 129b having an outer diameter greater than the inner diameter of the needle driver 128. Thus, the distal portion 129b limits the movement of the pusher 125 once inserted through the needle 120 and prevents the pusher 129 from falling into the lumen of the needle 120. The pusher 125 may include means for grasping a portion of the fastener during deployment. The means for grasping may be a pair of jaws attached to the distal end of the pusher 125, or a pair of split ends at the end of the pusher 125 that are configured to hold a fastener therebetween.

Tissue Fasteners

Figures 37A, 37B:
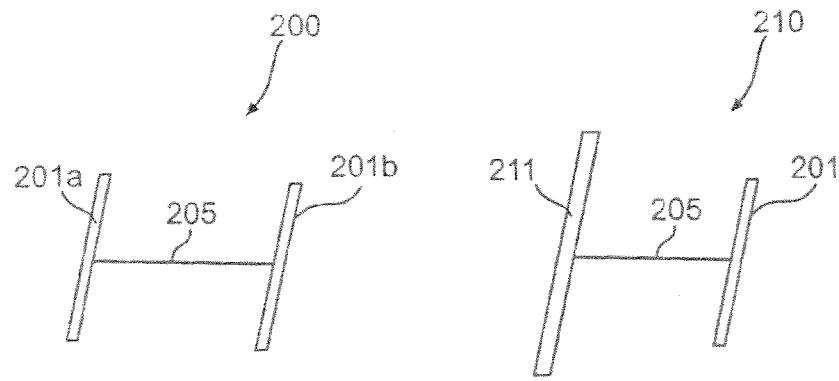
FIGS. 37A-37B are exemplary embodiments of double T-fasteners, according to various embodiments of the present invention.

With reference to FIGS. 37A-37B and FIGS. 38A-38C, various embodiments of a tissue fastener, according to the present invention, are described herein. FIGS. 37A and 37B show double T-fasteners 200, 210 having a proximal member 201a and a distal member 201b each connected to a connecting member 205, such as, for example, a suture, a bar, a coil, or a spring. The connecting member may be elastic to provide for self-adjustment. The fastener 200 shown in FIG. 37A has substantially identical members 201a, 201b on both ends of the connecting member 205. In an embodiment shown in FIG. 37B, the proximal member 211 on the esophageal side has a greater footprint than the distal member 201 on the stomach side. This acts to distribute forces on a larger area of the esophageal tissue. The proximal member 211 may have a smooth outer surface profile to minimize traumatization to a patient.

Figures 38A, 38B:
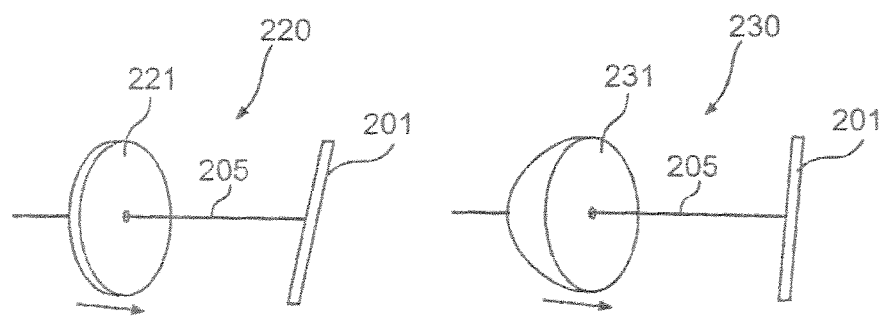
FIGS. 38A-38C are exemplary embodiments of adjustable button fasteners, according to various embodiments of the present invention.
Figure 38C:
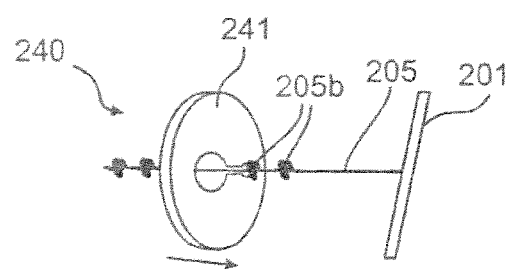

FIGS. 38A-38C show adjustable tissue fasteners, according to various embodiments of the present invention. The tissue fasteners 220, 230, 240 shown in the figures have proximal members 221, 231, 241 with greater footprints than those of the distal members 201. Furthermore, while the distal members 201 are fixedly attached to the distal end of the connecting member (such as a connecting member 205), the proximal members 221, 231, 241 are axially movable along the length of the connecting member 205, thereby allowing adjustment of the fastening tension between the distal and proximal members. Details descriptions of these embodiments are presented along with methods of fastening tissue layers further herein. Other various embodiments of a tissue fastener, such as the embodiments described in the commonly assigned U.S. application Ser. No. 10/230,672 of Robert DeVries et al. (U.S. Publication No. 2004/0044364 A1), the disclosure of which is hereby incorporated by reference, may alternatively be utilized.

Steps of Procedure

Figure 39:
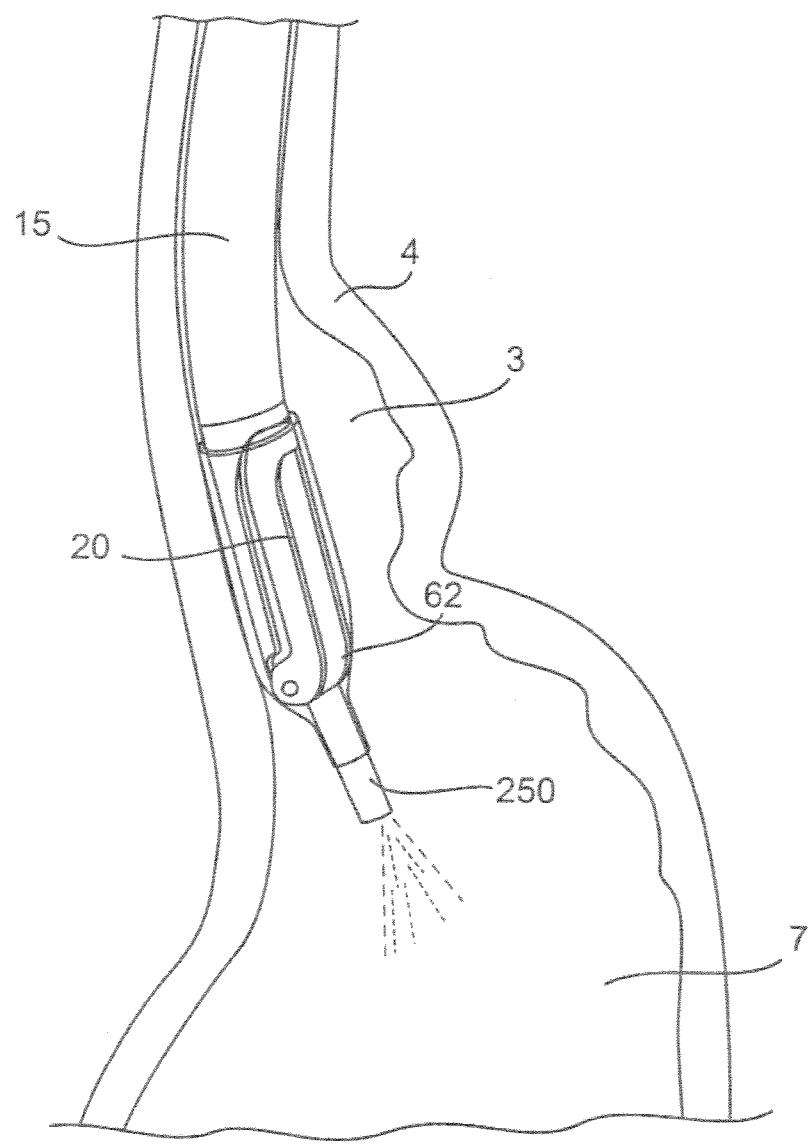
FIGS. 39-45 are schematic illustrations of an endoscopic tissue fastening method, according to an embodiment of the present invention.

With reference to FIGS. 39 through 46, an exemplary method of endoluminal fundoplication, according to an embodiment of the present invention, is described herein. FIG. 39 schematically illustrates the transoral insertion of the A-frame device 10 into the esophagus 3. During the insertion, protective sleeve 62 is provided to cover the A-frame head 20. Preferably, a suitable lubrication material is applied on the outer surface of the protective sleeve 62. The protective sleeve 62 protects the esophageal wall 4 from possible damage during the insertion. The protective sleeve 62 has an opening in its distal end for an endoscope 250 to protrude out of the sleeve 62 for viewing. It should be understood that other types of protective sleeves, such as, for example, embodiments shown in FIGS. 22 and 23, can be alternatively utilized.

Figure 40:
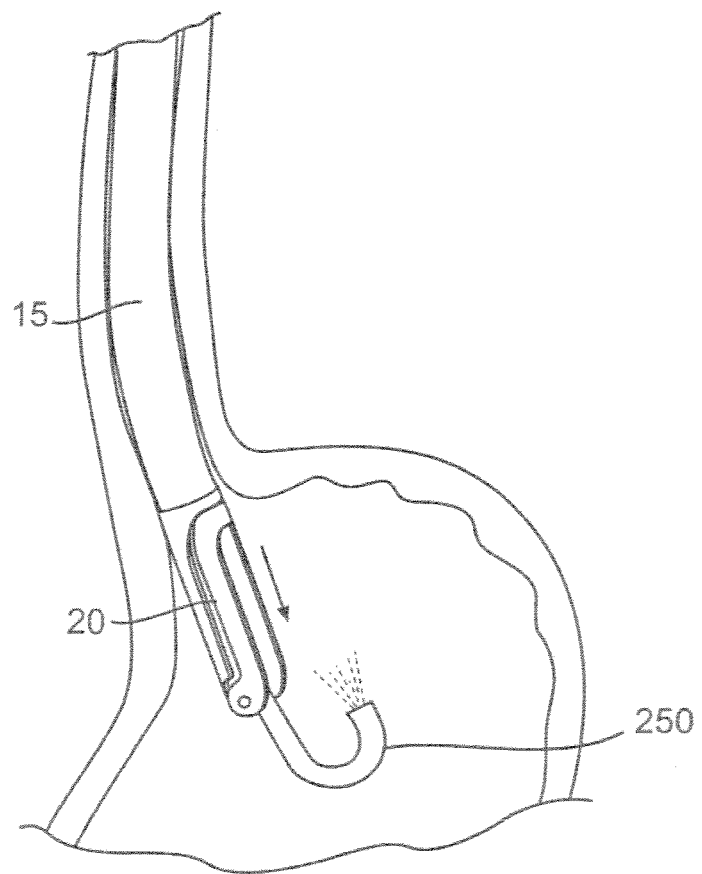
Figure 41:
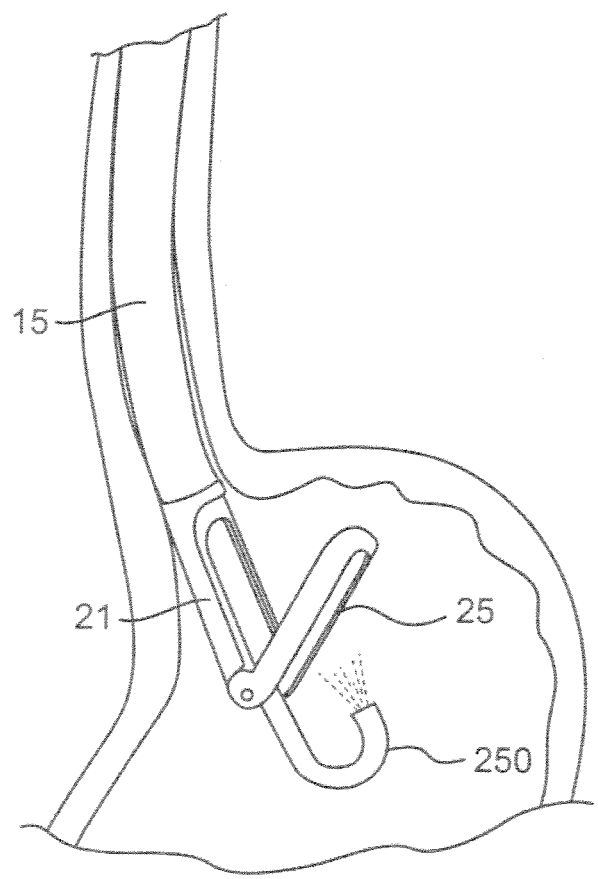

As shown in FIG. 40, once the A-frame head 20 is safely inserted into the gastro-esophageal junction site, the protective sleeve 62 is withdrawn from the A-frame head 20 through a working channel of the A-frame device 10. This may be achieved by pulling the handle of the protective sleeve 62 proximally, causing the sleeve 62 to invert and move into the working channel where it is withdrawn. The endoscope 250 is then retroflexed in the stomach 7 to view the A-frame head 20 and the working area. Once the A-frame head 20 is positioned in the stomach, the folding arm 25 of the A-frame head 20 is opened by using the A-frame handle 30 on the proximal end of the downtube 15, as shown in FIG. 41. The folding arm 25 extends in the stomach 7. The A-frame head then is properly positioned within the esophagus above the gastroesophageal junction.

Figure 42:
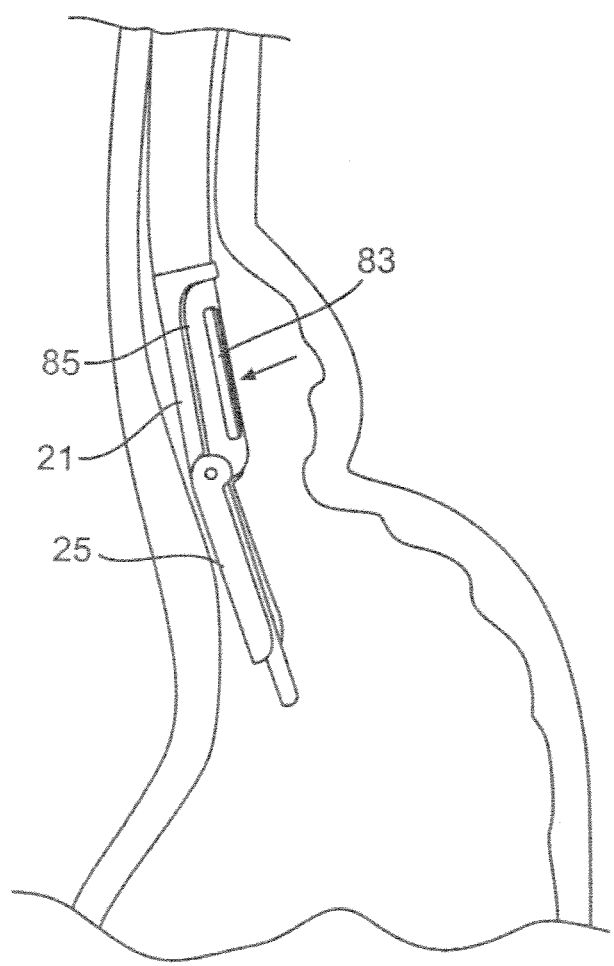
Figure 43:
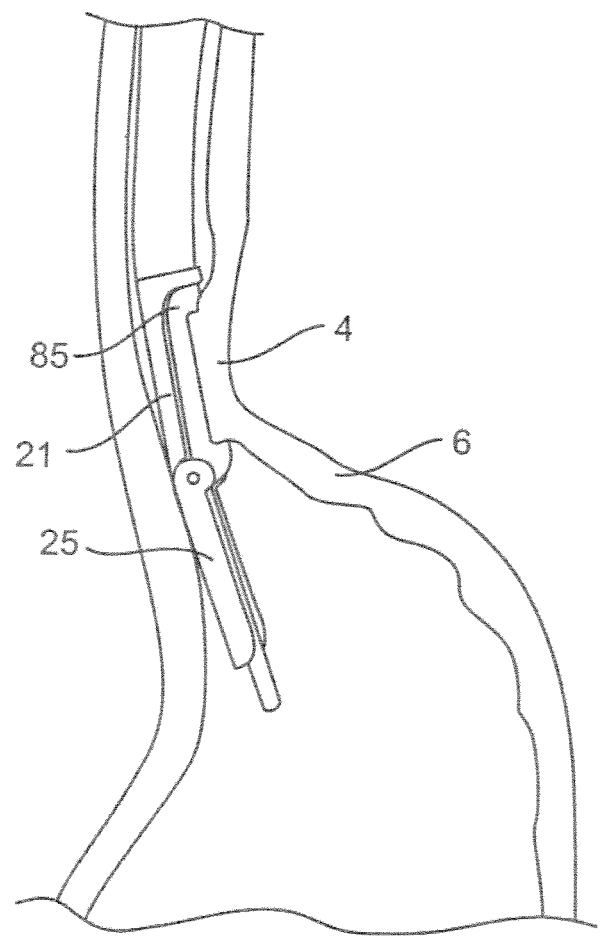

As shown in FIG. 42, when the A-frame head 20 is properly positioned with the folding arm opened, and the esophageal and fundus walls 4, 6 are ready to be folded, an invagination device, such as, for example, a grasper 85, is advanced into the A-frame overtube 15 and positioned proximate to the esophageal wall 4. A vacuum source (not shown) is then turned on and the suction force firmly grasps the esophageal wall 4, as shown in FIG. 43. The grasping of the esophageal wall 4 may be enhanced by activation of jaws 82a, 82b that may be placed in the vicinity of the suction opening 83 for holding the wall 4 more tightly when the suction is applied.

Figure 44:
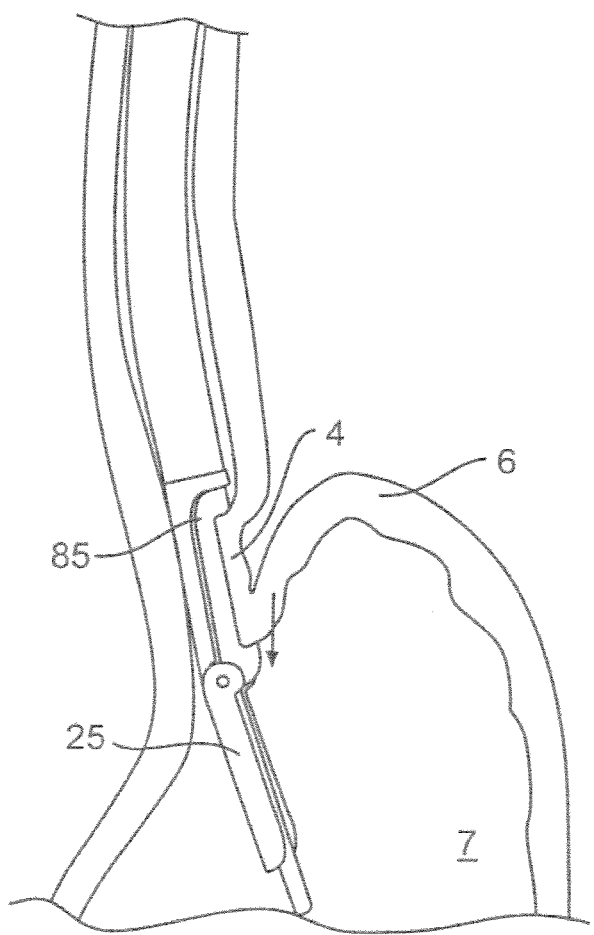
Figure 45:
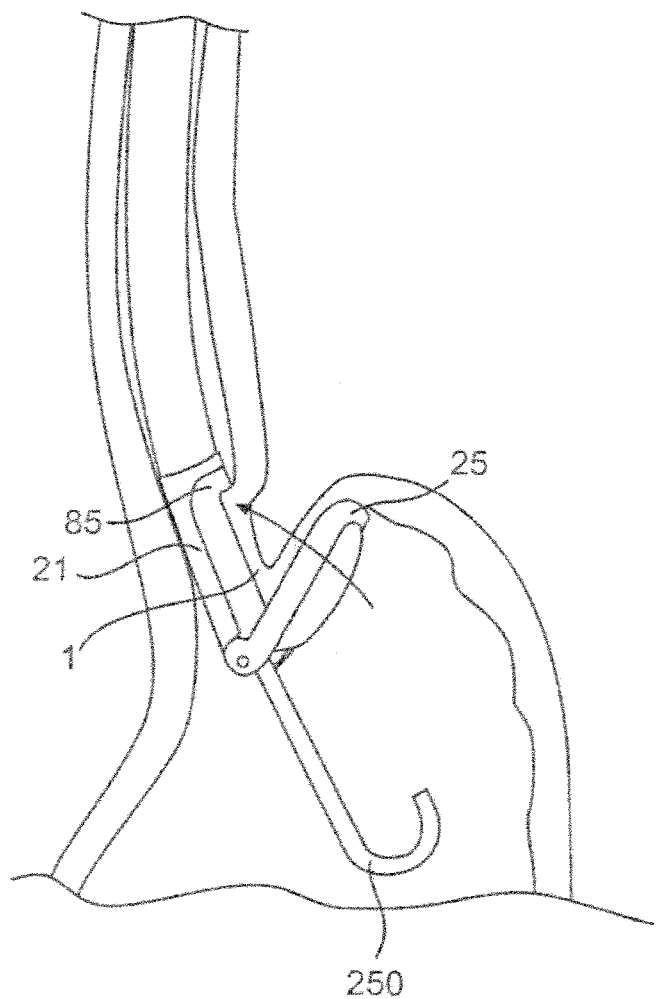

The firmly grasped esophageal wall 4 is then pushed down into the stomach 7 before the fundus wall of the stomach is folded proximate to the esophageal wall 4, as shown in FIG. 44. The folding arm 25 then closes and folds the fundus wall 6 proximate to the esophagus wall 4, creating a plicated fold 1, as shown in FIG. 45. While the folding arm 25 firmly holds the plicated fold 1, the vacuum from the grasper 85 and the grasp by the jaws 82a, 82b are released. The grasper 85, together with the jaws 82a, 82b, is then withdrawn from the A-frame head 20.

Figure 46:
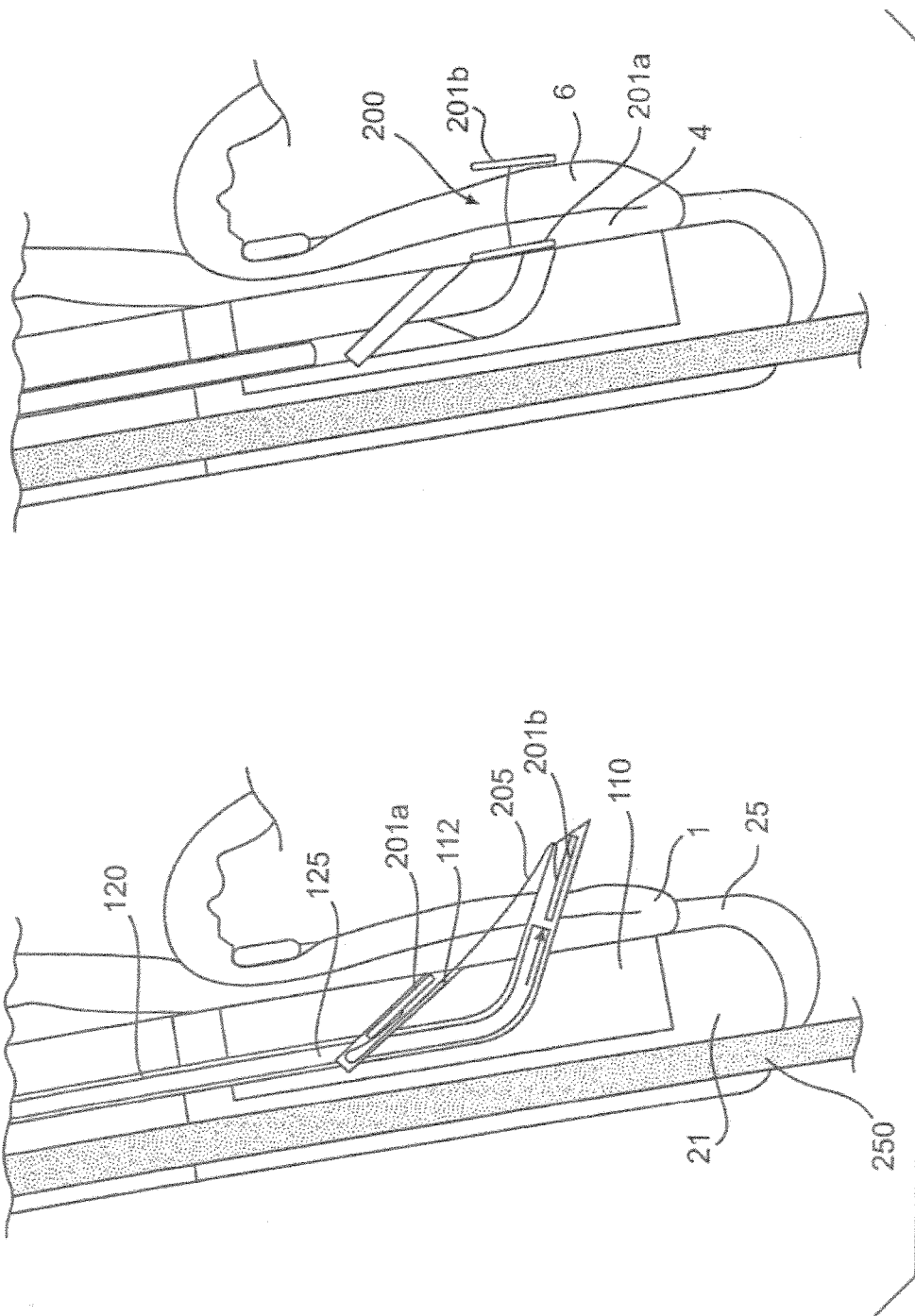
FIG. 46 is a schematic illustration of a method of fastening multiple tissue layers, according to an embodiment of the present invention.
Figure 47:
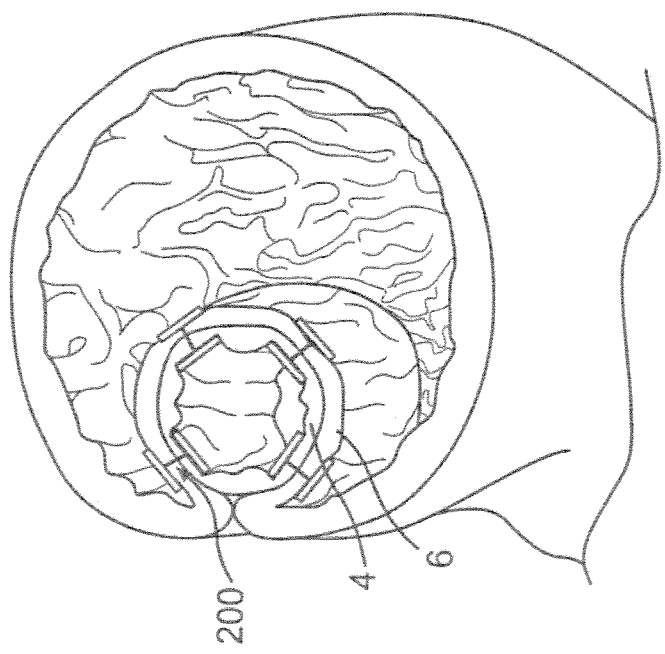
FIG. 47 is a perspective view of the gastrointestinal tract in the region of the lower esophageal sphincter (LES) and the fundus of the stomach, after a fundoplication procedure is performed with double T-fasteners.

A method of fastening a plicated fold 1 with a tissue fastener, according to an embodiment of the present invention, is described herein with reference to FIGS. 46-47. After creating a plicated fold 1 at the gastro-esophageal junction, a fastener delivery system 100, shown in FIGS. 32-36, is inserted into the working channel of the A-frame head 20. Prior to insertion into the A-frame device, the proximal member 201a of the tissue fastener 200 is placed on a fastener seat 112 formed on the outer top surface of the head 110 and the distal member 201b is placed inside the distal end portion of the needle 120.

As shown in FIG. 46, the delivery system 100 containing the double T-fastener 200 is advanced into the A-frame head 20 and placed proximate to the plicated fold 1, held by the folding arm 25. The needle 120 having a sharp cutting edge 121 is then guided along the internal groove 114 formed in the head 110 and perforates through the plicated fold 1, as shown in FIG. 46. Once the needle 120 passes through the plicated fold 1, the pusher 125 pushes the distal member 201b slight further into the stomach side, so that distal member 201b can extend out of the needle lumen and anchor against the fundus wall 6. Since the distal member 201b is fixedly attached to the distal end of the connecting member 205 with a predetermined length, the proximal member 201a falls out of the fastener seat 112 and anchors against the esophageal side wall 4, as shown in the right figure of FIG. 46. Depending on, among other things, the type of tissue fasteners used and the desired fastening strength, additional tissue fasteners 200 may be placed by repeating the method described above. In general, the entire A-frame device 10 is rotatable and axially displaceable within the esophagus for placing another fastener. In addition, only the fastener delivery system can be moved relative to the A-frame device 10. FIG. 47 shows the gastro-esophageal junction with a plurality of double T-fasteners 200 in place. In this embodiment, the connecting member 205 has a predetermined fixed length.

Figure 48:
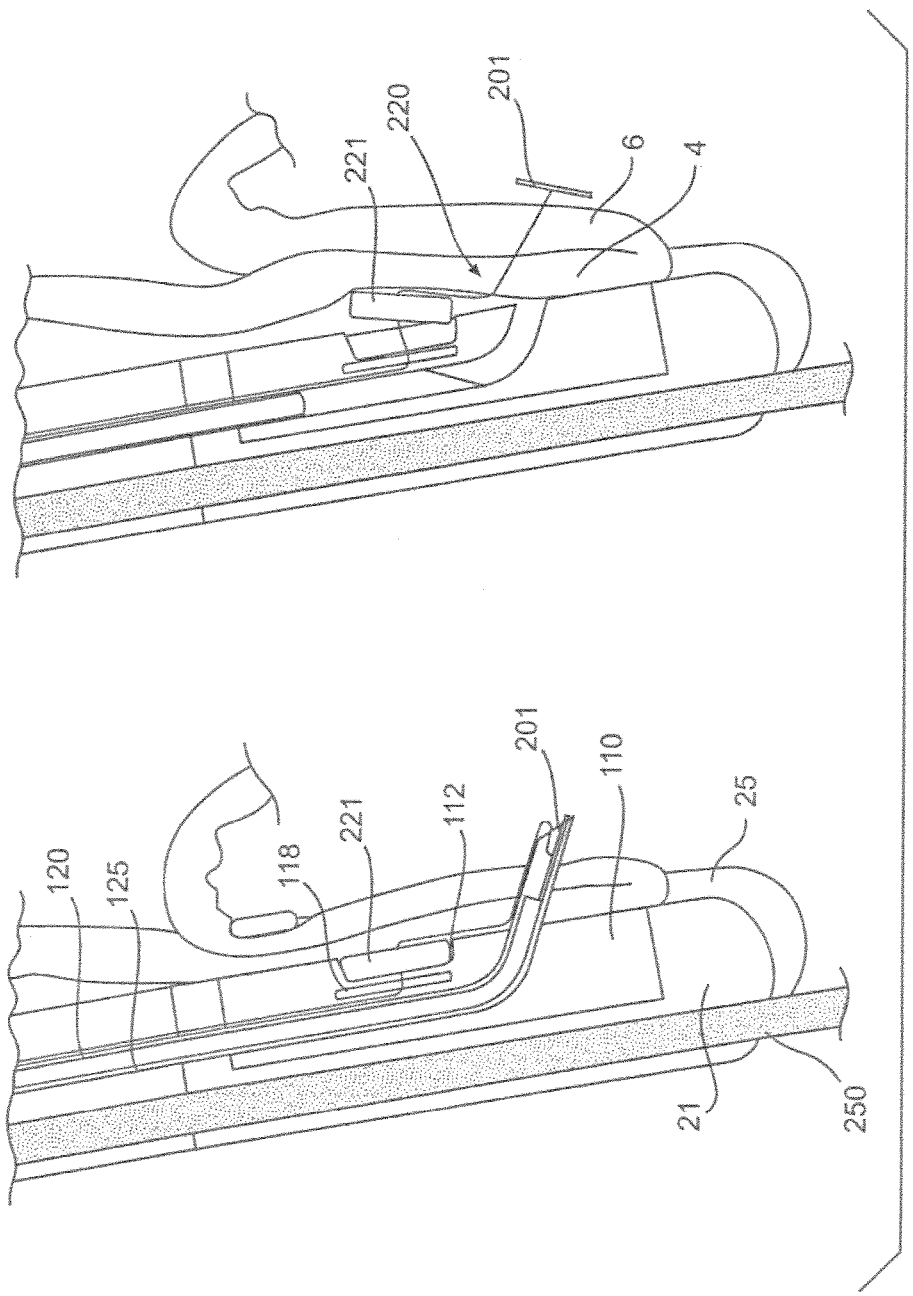
FIGS. 48-49 are schematic illustrations of a method of fastening multiple tissue layers, according to another embodiment of the present invention.
Figure 49:
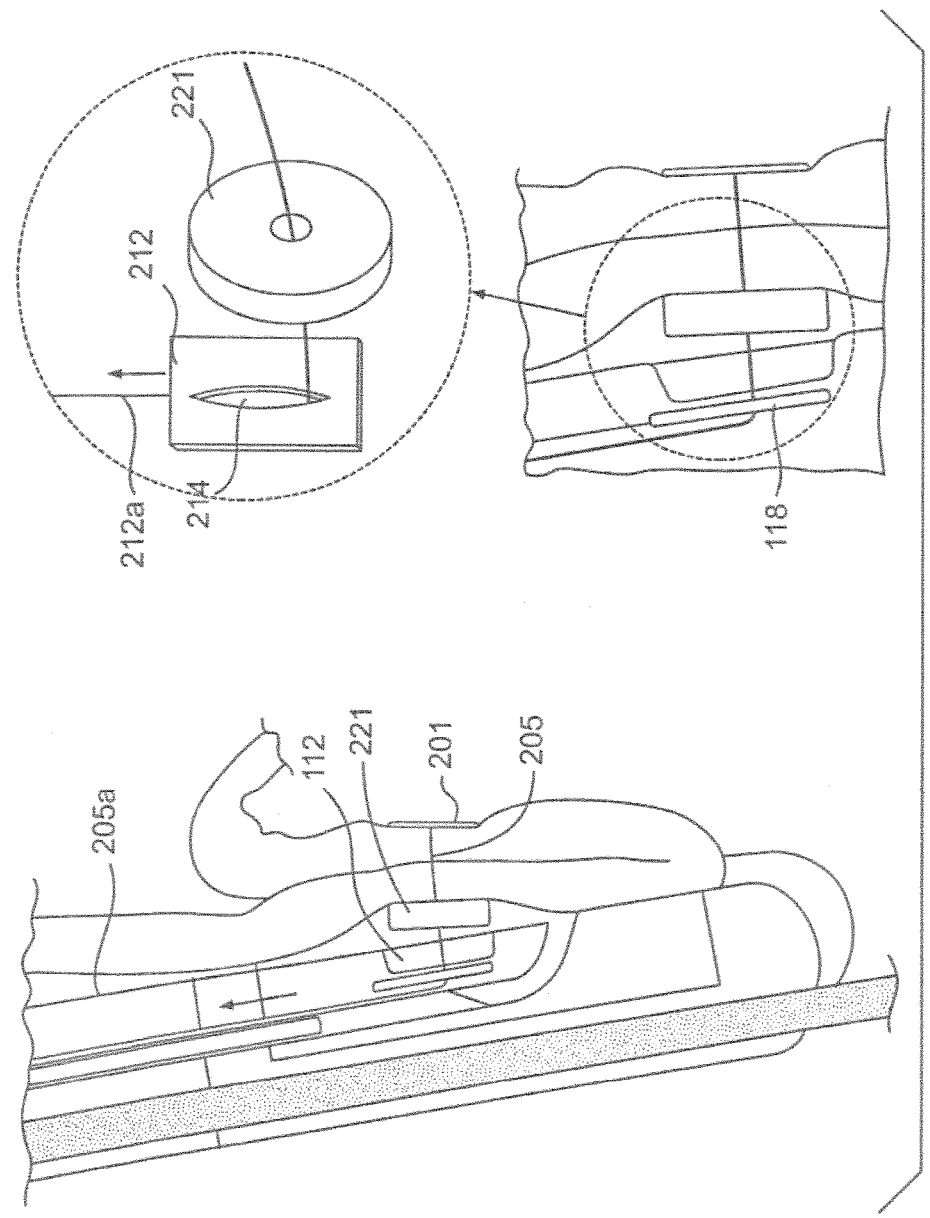
Figure 50:
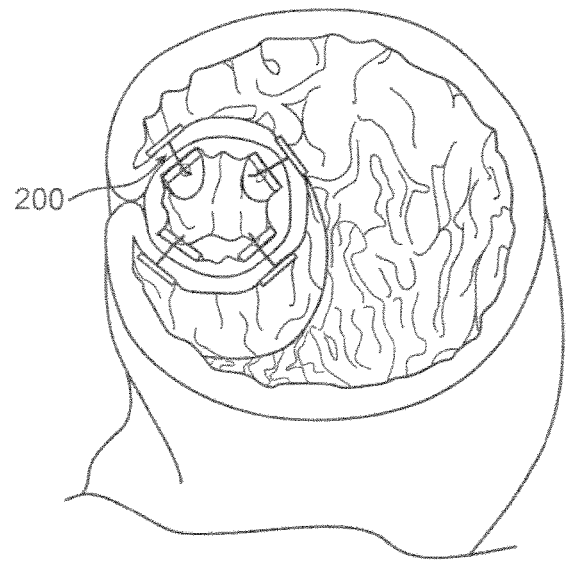
FIGS. 50-52 are perspective views of the gastrointestinal tract in the region of the lower esophageal sphincter (LES) and the fundus of the stomach, after a fundoplication procedure is performed with various embodiments of the tissue fasteners shown in FIGS. 38A, 38B, and 38C, respectively.

FIGS. 48-50 schematically illustrate a method of fastening the plicated fold 1 with a tissue fastener 220, according to another embodiment of the present invention. Similar to the embodiment shown in FIGS. 46-47, prior to insertion into the A-frame device 10, the proximal member 221 of the tissue fastener 220 is placed on a fastener seat 112 formed on the outer top surface of the head 110 and the distal member 201 is placed inside distal end portion of the needle 120. Preferably, the distal member 201 has interference fit with the inner surface of the needle 120 so that the distal member 201 does not fall out of the needle 120. Alternatively, the pusher 125 has a grasping means at its distal end to hold the distal member 201.

The operational procedures are substantially identical with the method illustrated in FIGS. 46-47, except that the this procedure involves an adjustable fastener and that the proximal member of the fastener has a greater footprint than that of the distal member. For example, while the distal member 201 is fixedly secured to a distal end of the connecting member 205, the proximal member 221 is axially movable along the length of the connecting member 205 and, thereby, the fastening tension can be adjusted. The connecting member 205 may extend outside of a body or connects to a suitable grasper-pusher device that extends outside of the body. Preferably, the proximal member 221 is movable only in a direction toward the distal member 201.

As shown in FIG. 48, once the needle 120 and the tissue fastener 220 are brought proximate to the plicated fold 1, the needle 120 perforates through the plicated fold 1, carrying the distal member 201 of the fastener 220 into the stomach side 7. After the distal member 201 falls into the stomach side 7, the proximal member 221 falls out of the fastener seat 112 and loosely faces against the esophageal side wall 4, as shown in the right figure of FIG. 48. The proximal end 205a of the connecting member 205 is then pulled back to tighten the tension between the distal and proximal members 221, 201 of the fastener, as shown in the right-hand portion of FIG. 49.

After the tension is adjusted as desired, any excess connecting member 205a beyond the proximal member 221 is cut by a blade member 212 disposed in an internal slot 118 formed in the head 110. In this embodiment, the blade member 212 has an eye-shaped opening 214 through which the connecting member 205 passes behind the proximal member 212. Preferably, prior to the insertion of the delivery system 200 in the A-frame device 10, the blade member 212 is placed in the internal slot 118, and the proximal member 221 of the fastener 220 is placed in the fastener seat 112 with the connecting member 205 behind the proximal member 221 passing through the opening 214 of the blade member 212, as shown in FIG. 49. At least a portion of the opening peripheral edge has a sharpened edge for cutting the excess connecting member 205a. Activation of the blade member 212 can be achieved by any suitable proximal activation device attached to the blade member 212 by a wire, cable, or other like mechanisms 212a. FIG. 50 shows the gastroesophageal junction with a plurality of button fasteners 220 in place.

Figure 51:
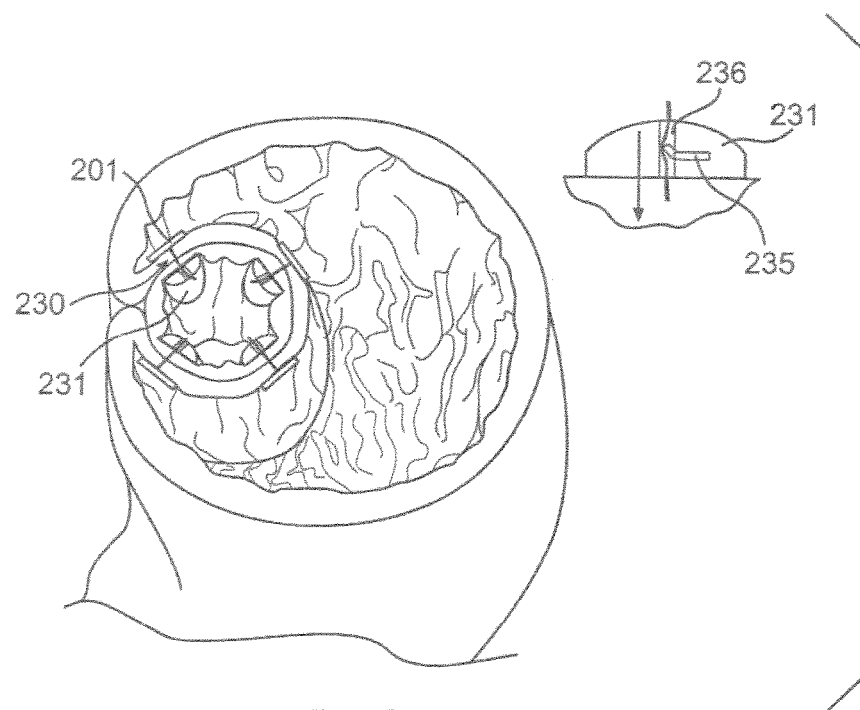

FIG. 51 shows the gastro-esophageal junction with a plurality of dome-shaped button fasteners 230 in place, according to still another embodiment of the present invention. The dome-shaped button fastener 230 provides enhanced buttressing effect. This fastener 230 is also tension-adjustable and includes a tab 235 to adjust the tension of the connecting member 205. Preferably, the tab 235 rests on the proximal member 231 of the faster 230 and is closes the opening 236 in the proximal member 231, through which the connecting member 205 passes. Thus, once the connecting member 205 is pulled, the tab 235 slightly opens the opening. Once the desired tension is achieved, the connecting member 205 is released and the tab 235 secures the movement of the proximal member 231 relative to the connecting member. Alternatively, the connecting member 205 may include other suitable friction means, such as, for example, bumps and notches, that is configured to interfere with the tab 235 and allow displacement in only one direction, preferably to the proximal side (see arrow in FIG. 51).

Figure 52:
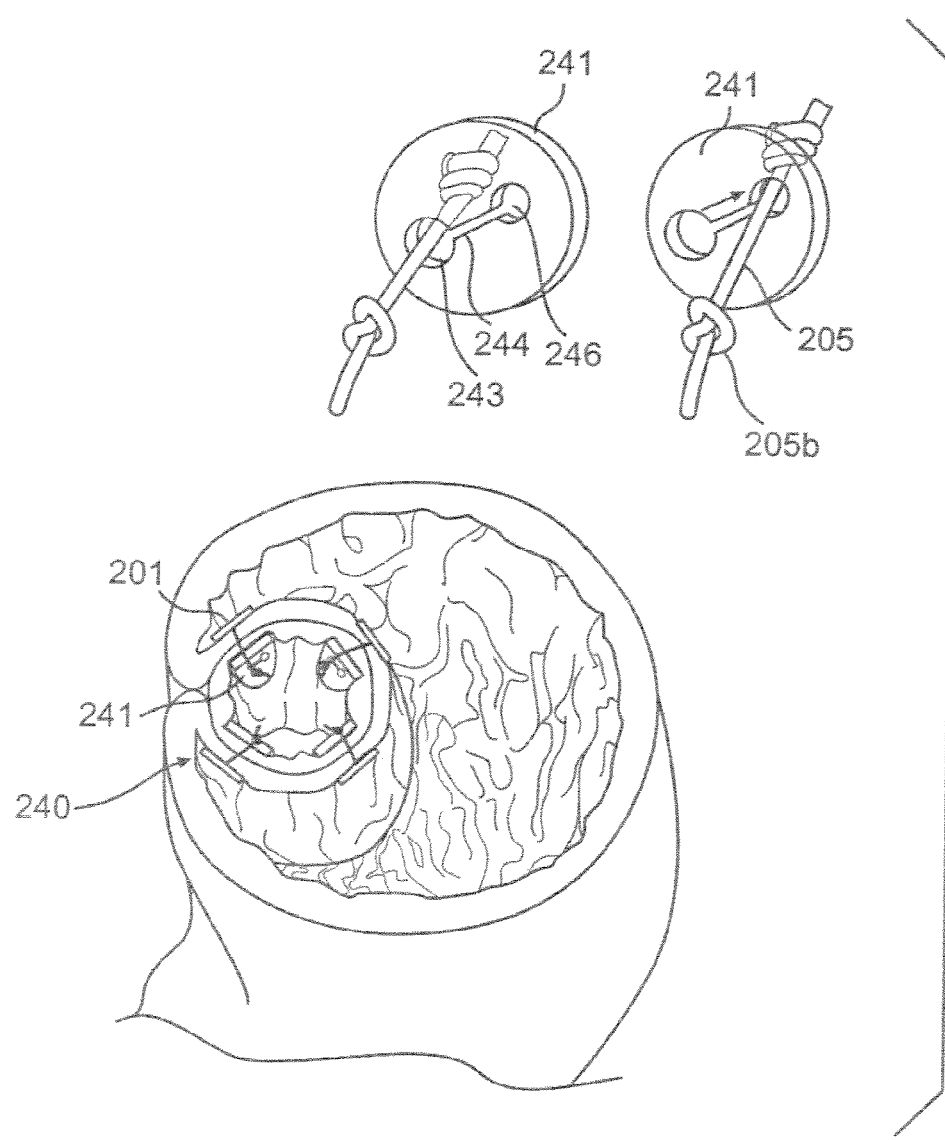

FIG. 52 shows the gastro-esophageal junction with a plurality of button fasteners 240 in place, according to yet another embodiment of the present invention. The proximal member 241 of the fastener 240 has first and second openings 243, 246 with a slot 244 communicating between the two openings 243, 246. The connecting member 205 includes a plurality of knots 205b, each separated preferably with an uniform interval, though knots 205b can be separated by any desired uniform or non-uniform interval. The area of the first opening 243 is large enough to allow the knots 205b to freely pass through the opening 243, while the area of the second opening 245 is smaller than the outer diameter of the knots 205b so as not to allow the passage of the knots 205b through the opening 245. The opening of the slot is only slightly larger than the diameter of the connecting member 205. In operation, the connecting member 205 having a plurality of knots 205b is positioned in the first opening 243 and adjusted to achieve a desired level of tension between the distal and proximal members 201, 241 in the connecting member 205. Once the desired tension is achieved, the connecting member 205 is transferred to the second opening 246 to hold the corresponding knot 205b against the proximal member 241.

Other suitable designs of tissue fasteners having the similar operational characteristics may be utilized. Moreover, the disclosed tissue fasteners 200, 210, 220, 230, 240 may be used with any other suitable deployment mechanisms known in the art.

Although the present invention is depicted in this disclosure as being used in the treatment of GERD, e.g., a fundoplication procedure performed in the gastro-esophageal junction, it is to be understood that the tissue fastener and related deployment methods and systems of the present invention can be used to treat any of a number of different disease conditions, and can be used for fastening any desired body tissues.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for fastening tissue, the system comprising:
a tubular member having a proximal end and a distal end, wherein the distal end is coupled to a first arm configured to pivot with respect to the tubular member to receive tissue;
a grasper configured for positioning proximate the distal end of the tubular member for grasping tissue; and
a fastener configured for insertion into the tissue, the fastener having a connecting member, a proximal fastening member, and a distal fastening member, wherein the connecting member connects the proximal fastening member to the distal fastening member, and wherein the fastener is adjustable between at least two implantation configurations, the at least two implantation configurations including: a) the connecting member having a first length between the proximal and distal members, and b) the connecting member having a second length between the proximal and distal members, wherein the second length is different than the first length,
wherein the tissue fastener is configured for delivery to the tissue through a lumen of the tubular member.

2. The system of claim 1, wherein the distal end of the tubular member includes a second arm, and wherein tissue is received between the first arm and the second arm.

3. The system of claim 1, wherein one of the proximal or distal fastening members is attached to a portion of the connecting member, and the other of the proximal or distal fastening members is movably coupled to the connecting member proximate the portion of the connecting member.

4. The system of claim 3, wherein the fastener includes at least one element configured to prevent movement of the other of the proximal fastening member or the distal fastening member along the connecting member.

5. The system of claim 4, wherein the at least one element includes a knot adjacent to the proximal fastening member or the distal fastening member.

6. The system of claim 4, wherein the at least one element is configured to prevent movement of the proximal fastening member or the distal fastening member in only one direction.

7. The system of claim 1, wherein the grasper is translatable relative to the distal end of the tubular member.

8. The system of claim 1, wherein the grasper includes jaws.

9. The system of claim 1, further comprising a needle, wherein at least a portion of the fastener is coupled to the needle.

10. A system for fastening tissue, the system comprising:
a tubular member having a proximal end and a distal end, wherein the distal end includes a first arm and a second arm, the first arm configured to pivot with respect to the second arm to receive tissue therebetween, wherein, when the first arm is in an open position relative to the second arm, a proximal-most end of the first arm is rotatably coupled to a distal end of the second arm;
a grasper configured for translation relative to the distal end of the tubular member for grasping tissue; and
a fastener configured for insertion into the tissue, the fastener having a connecting member, a proximal fastening member, and a distal fastening member, wherein the connecting member connects the proximal fastening member to the distal fastening member, and wherein the fastener is adjustable between at least two implantation configurations, the at least two implantation configurations including: a) the connecting member having a first length between the proximal and distal members, and b) the connecting member having a second length between the proximal and distal members, wherein the second length is different than the first length.

11. The system of claim 10, further comprising a needle, wherein the first arm or the second arm includes a slot for receiving the needle.

12. The system of claim 11, wherein at least a portion of the fastener is disposed within the needle.

13. The system of claim 10, wherein the fastener is adjustable by moving at least one of the proximal fastening member or the distal fastening member with respect to the other of the proximal fastening member or the distal fastening member.

14. The system of claim 13, wherein the proximal fastening member has a same shape as a shape of the distal fastening member.

15. The system of claim 10, wherein the fastener comprises an elastic material.

\* \* \* \* \*